United States Patent [19]

Fumio et al.

[11] Patent Number: 4,468,521

[45] Date of Patent: Aug. 28, 1984

[54] METHOD OF PRODUCING GAMMA-HALOGENO-DELTA UNSATURATED CARBOXYLIC ACID ESTERS

[75] Inventors: Mori Fumio, Kurashiki; Omura Yoshiaki, Mitsu; Nishida Takashi, Kurashiki; Itoi Kazuo, Kitakanbara, all of Japan

[73] Assignee: Kuraray Co., Ltd., Kurashiki, Japan

[21] Appl. No.: 350,566

[22] Filed: Feb. 22, 1982

Related U.S. Application Data

[60] Continuation of Ser. No. 840,279, Oct. 7, 1977, abandoned, which is a division of Ser. No. 705,176, Jul. 14, 1976, abandoned.

[30] Foreign Application Priority Data

Jul. 22, 1975 [JP] Japan ..................... 50-89507
Dec. 29, 1975 [JP] Japan ..................... 50-158047
Apr. 30, 1976 [JP] Japan ..................... 51-50595

[51] Int. Cl.$^3$ ............................................. C07C 69/743
[52] U.S. Cl. ................................. 560/124; 260/465 D; 548/477; 548/478; 548/513; 548/517; 548/527; 548/547; 548/562; 549/60; 549/66; 549/77; 549/79; 549/478; 549/491; 549/499; 560/217; 560/219
[58] Field of Search ............... 560/124, 211, 217, 219; 562/506; 260/465 D; 548/477, 478, 513, 517, 527, 547, 562; 549/60, 66, 77, 79, 478, 491, 499

[56] References Cited

U.S. PATENT DOCUMENTS

| | | | |
|---|---|---|---|
| 3,077,496 | 2/1963 | Julia | 560/124 |
| 3,123,629 | 3/1964 | Julia | 560/124 |
| 3,354,196 | 11/1967 | Julia | 560/124 |
| 3,652,652 | 3/1972 | Julia | 560/124 |
| 4,083,855 | 4/1978 | Itaya | 560/124 |

FOREIGN PATENT DOCUMENTS

| | | | |
|---|---|---|---|
| 2539895 | 3/1976 | Fed. Rep. of Germany | |
| 2621835 | 11/1976 | Fed. Rep. of Germany | 560/124 |
| 7605172 | 11/1976 | Netherlands | |

*Primary Examiner*—Michael L. Shippen
*Attorney, Agent, or Firm*—Burns, Doane, Swecker & Mathis

[57] ABSTRACT

Novel γ-lactone derivatives are provided. These lactone derivatives, when reacted with hydrogen halide in alcohol, yield γ-halogeno-δ-unsaturated carboxylic acid esters. This ring-opening process is useful for the purpose of increasing the yield of pyrethrin analogs which are of value as insecticides and agricultural chemicals. Thus, the γ-lactone derivatives by-produced in the production process for dihalogenovinyl chrysanthemumates are caused to undergo ring-opening reaction to yield the corresponding γ-halogeno-δ-unsaturated carboxylic acid esters which are important intermediates for said pyrethrin analogs.

19 Claims, No Drawings

METHOD OF PRODUCING GAMMA-HALOGENO-DELTA UNSATURATED CARBOXYLIC ACID ESTERS

This application is a continuation of application Ser. No. 840,279, filed Oct. 7, 1977, now abandoned, which in turn is a division of application Ser. No. 705,176, filed July, 14, 1976 now abandoned.

The present invention relates, in one aspect, to novel γ-lactone derivatives which can be converted to γ-halogeno-δ-unsaturated carboxylic acid esters of value as intermediates for the synthesis of substituted cyclopropanecarboxylic acid esters and, in another aspect, to a method for producing said γ-halogeno-δ-unsaturated carboxylic acid esters from said γ-lactone derivatives.

A principal object of the present invention is to provide a method whereby the γ-lactone derivatives by-produced in the production process for dihalogenovinyl chrysanthemumates, which are currently attracting much attention as insecticides and agricultural chemicals, are permitted to undergo a ring-opening reaction to yield the corresponding γ-halogeno-δ-unsaturated carboxylic acid esters. Another object is to increase the yield of cyclopropanecarboxylic acid esters for dihalogenovinyl chrysanthemumates by means of said method, as will hereinafter be described in detail.

The γ-lactone derivatives according to the present invention are represented by the following general formula (I):

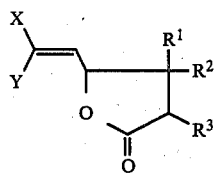
(I)

(wherein $R^1$ and $R^2$, respectively, mean a lower alkyl group of 1 to 5 carbon atoms; $R^3$ is selected from the class consisting of hydrogen, alkyl groups of 1 to 5 carbon atoms and cycloalkyl groups of 3 to 8 carbon atoms; Y is X or —CHX—CH$_3$; and Xs are the same or different halogen atoms).

Referring to general formula (I), $R^1$ and $R^2$, respectively, mean a lower alkyl group of 1 to 5 carbon atoms, being preferably methyl, ethyl, propyl or neopentyl. $R^3$ is a hydrogen atom, an alkyl group of 1 to 5 carbon atoms or a cycloalkyl group of 3 to 8 carbon atoms, preferably hydrogen, methyl, ethyl, propyl or cyclohexyl. X is chlorine, bromine, fluorine or iodine, preferably a chlorine or bromine atom. Y is said X or —CHX—CH$_3$, preferably chlorine, bromine, 1-chloroethyl or 1-bromomethyl.

When the ease of conversion to the corresponding γ-halogeno-δ-unsaturated carboxylic acid esters and the ease of conversion to cyclopropanecarboxylic acid esters for dihalogenovinyl chrysanthemumates are taken into consideration, the preferred members of the γ-lactone derivative of general formula (I) are those γ-lactone derivatives which may be represented by the following general formula (I'):

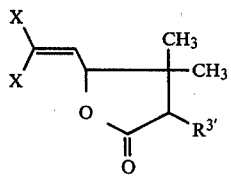
(I')

(wherein X has the same meaning as defined for general formula (I); $R^{3'}$ is a member of the class consisting of hydrogen and alkyl groups of 1 to 5 carbon atoms). Typical species of the preferred γ-lactone derivatives are as follows.

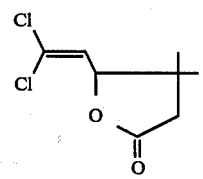
3,3-Dimethyl-4-(2',2'-dichlorovinyl)-4-butanolide

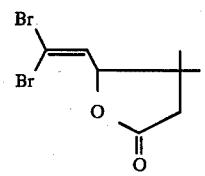
3,3-Dimethyl-4-(2',2'-dibromovinyl)-4-butanolide

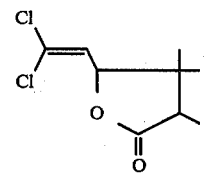
2,3,3-Trimethyl-4-(2',2'-dichlorovinyl)-4-butanolide

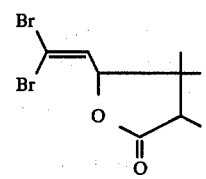
2,3,3-Trimethyl-4-(2',2'-dibromovinyl)-4-butanolide

In the present invention, a γ-lactone derivative of general formula (I) is reacted with a hydrogen halide and an alcohol having the following general formula (II):

$R^4OH$ (II)

to obtain a γ-halogeno-δ-unsaturated carboxylic acid ester of the following general formula (III):

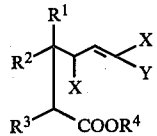
(III)

easily and in high yield. (Referring to the above general formulas (II) and (III), $R^4$ is an alcohol residue; and $R^1$, $R^2$, $R^3$, X and Y in general formula (III) have the same meanings as respectively defined for general formula (I)).

As examples of the alcohol ($R^4OH$) used herein, there may be mentioned the alcohols whose residues $R^4$ (i.e.

the residue after removal of a hydroxyl group from each alcohol) are alkyl groups, cycloalkyl groups, alkenyl groups, cycloalkenyl groups, alkynyl groups,

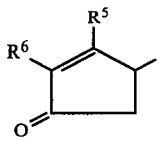

(wherein $R^5$ is hydrogen or methyl; $R^6$ is alkenyl, alkadienyl, alkynyl or benzyl),

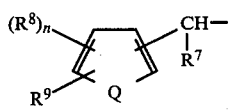

(wherein $R^7$ is hydrogen, ethynyl or cyano; $R^8$ is hydrogen, halogen or alkyl; $R^9$ is halogen, alkyl, alkenyl, alkynyl, benzyl, thenyl, furylmethyl, phenoxy or phenylthio; $R^8$ and $R^9$, taken together, may represent a polymethylene group which may optionally be interrupted by a sulfur or oxygen atom; Q is —O—, —NH—, —S— or —CH=CH—; n is 1 or 2), A—CH$_2$— (wherein A is phenoxyphenyl, phthalimido, thiphthalimido, di- or tetrahydrophthalimido or dialkylmaleimide),

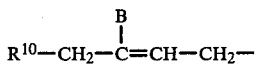

(wherein $R^{10}$ is phenyl, thienyl or furyl; B is halogen) and so forth. Preferred are alcohols whose residues are lower alkyl groups such as methyl and ethyl. More particularly, there may be mentioned methanol, ethanol, propanol, butanol, octanol, benzyl alcohol, 3-phenoxybenzyl alcohol, allethrolone, pyrethrolone, 5-benzyl-3-furylmethyl alcohol, 5-phenoxyfurfuryl alcohol, 4-phenyl-2-butyn-1-ol and so forth, although lower alcohols such as methoanol, ethanol, propanol, butanol, etc. are especially desirable. The amount of such alcohol may be at least 0.5 times the stoichiometric amount necessary for the ring-opening esterification of γ-lactone derivative (I). However, generally 0.5 to 10 molecular equivalents and preferably 1.5 to 7 molecular equivalents of the alcohol is employed. If desired, the alcohol may be used in large excess, e.g. 10 molecular equivalents or more, so that it may act also as the solvent.

As the hydrogen halide, there may be mentioned hydrogen chloride, hydrogen bromide, hydrogen iodide and hydrogen fluoride, although hydrogen chloride and hydrogen bromide are preferred.

The amount of said hydrogen halide may range from 0.5 to 10 times the stoichiometric amount necessary for the ring-opening reaction of γ-lactone derivative (I), the range of 1.3 to 5 molecular equivalents being preferred.

This reaction may be carried out in an open system or in a closed system, within the temperature range of 0° to 150° C. Where the amount of hydrogen halide is not less than about twice the stoichiometric amount necessary for the ring-opening reaction of γ-lactone derivative (I), quite satisfactory results may be obtained by conducting the reaction at a temperature between 0° C. and room temperature (about 30° C.) and in an open system. Where the amount of hydrogen halide is less than twice said stoichiometric amount, the reaction is preferably conducted in a closed system at a temperature in the range of 50° to 100° C.

In conducting this ring-opening esterification reaction, the reactor may be charged with the starting material γ-lactone derivative, hydrogen halide and alcohol in an optional order but it is preferable either: (A) to let the hydrogen halide be absorbed into the alcohol and, then, add the starting material γ-lactone derivative to the solution or (B) to add the hydrogen halide to a mixture of the alcohol and starting material γ-lactone derivative.

After the reaction has been completed, the reaction mixture may be directly subjected to distillation to recover the excess hydrogen halide and alcohol. Then, the residue may be further distilled under reduced pressure to obtain the contemplated γ-halogeno-δ-unsaturated carboxylic acid ester.

The γ-halogeno-δ-unsaturated carboxylic acid ester of general formula (III) is especially of value as intermediates for the synthesis of cyclopropanecarboxylic acid esters for dihalogenovinyl chrysanthemumates having strong insecticidal activity. Thus, by treating a γ-halogeno-δ-unsaturated carboxylic acid ester of general formula (III) with an organic or inorganic basic reagent, there can be produced a cyclopropanecarboxylic acid ester of the following general formula (IV):

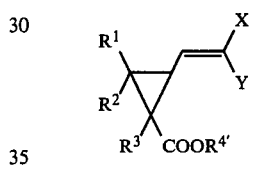

Referring to the above general formula (IV), $R^1$, $R^2$, $R^3$, X and Y have the same meanings as respctively defined for general formula (I) and $R^{4'}$ is an alcohol residue which may be either the same as or different from $R^4$, provided that even where $R^{4'}$ is an alcohol residue different from $R^4$, the former alcohol residue is preferably one of those mentioned for $R^4$.

As examples of the basic reagent used as above, there may be mentioned alkali metal hydroxides such as sodium hydroxide, potassium hydroxide, etc.; alkali metal alcoholates such as sodium methylate, sodium ethylate, potassium methylate, potassium ethylate, sodium n-propylate, sodium n-butylate, sodium t-butylate, sodium isoamylate, potassium t-butylate, potassium isoamylate, etc.; nitrogen-containing organic bases such as 1,5-diazabicyclo[3,4,0]nonene-5 (DBN), 1,5-diazabicyclo[5,4,0]undecene-5(DBU), 1,4-diazabicyclo[2,2,2]octane(DABCO), 2-dimethylamino-1-pyrroline, 5-methyl-1-azabicyclo[3,3,0]octane, etc.; organolithium compounds such as n-butyllithium, sec-butyllithium, diisopropylaminolithium, dicyclohexylaminolithium, etc.; sodium hydride, sodium amide, sodium metal, etc.; by way of example. Treatment with such a basic reagent may generally be carried out at a temperature between about −80° C. and about 150° C. but where an alkali metal alcoholate, alkali metal hydroxide or a nitrogen-containing organic base is employed, this treatment is preferably carried out at about 0° C. to about 100° C. or when sodium hydride or sodium amide, for instance, is employed, the preferred temperature range is from −70° C. to about 25° C. This treatment with a basic reagent does not always require the use of a solvent but, if desired, use may be made of a solvent inert to the reaction or a solvent which does not interfere with the reaction, such as ethyl ether, tetrahydrofuran, benzene, chlorobenzene, toluene, methanol, ethanol, propanol, butanol, n-hexane, n-octane, carbon tetrachloride, methylene chloride, ethyl acetate, acetonitrile or the like. Generally, the basic reagent is used preferably in a proportion of about 0.3 mole to about 7 moles per mole or starting material ester, but when a nitrogen-containing organic base is employed, it may be used in large excess so that it will act also as the solvent.

The cyclopropanecarboxylic acid ester which is produced upon treatment with such a basic reagent does not always possess the same alcohol residue as that of the starting material ester used in the treatment with basic reagent but when an alcohol not corresponding to the alcohol residue in the starting material ester is used as the solvent, for instance, there is normally produced a cylcopropanecarboxylic acid ester possessing the alcohol residue derived from the solvent alcohol as the result of transesterification with the solvent alcohol. Also, where an alkali metal alcoholate is employed as the basic reagent, there may be produced a cyclopropanecarboxylic acid ester possessing the alcohol residue derived from said alkali metal alcoholate.

Cyclopropanecarboxylic acid esters of general formula (IV) are insecticides or synthetic intermediates thereof. The allethronyl ester, pyrethronyl ester, 3-phenoxybenzyl ester, 5-benzyl-3-furylmethyl ester, etc. of 2,2-dimethyl-3-(2',2'-dihalogenovinyl) cyclopropanecarboxylic acid, in particular, are insecticidally more than several times as active as the corresponding esters of crysanthemummonocarboxylic acid, their stability against light being also higher. These compounds, in fact, are pyrethrin analogs which are currently attracting much attention (European Chemical News, November 23, 39 (1973); M. Elliot et al, Nature 244, 456 (1973); D. G. Brown et al, J. Agr. Good Chem. 21, No. 5, 767 (1973)).

Heretofore known, for the production of lower alkyl esters of 2,2-dimethyl-3-(2',2'-dihalogenovinyl) cyclopropanecarboxylic acids, is a method in which a lower alkyl ester of 3-formyl-2,2-dimethylcyclopropanecarboxylic acid which is obtainable by ozonolysis of the lower alkyl ester of chrysantemummonocarboxylic acid is subjected to Wittig reaction (Japanese Patent Application Laid Open No. 47531/1974, corres. to German Pat. Laid Open No. 2326077) but this method is not commerically advantageous partly because the starting material chrysanthemummonocarboxylic acid lower alkyl ester is expensive and partly because the method involves the use of a costly phsophorus compound.

Farkas et al added a diazoacetic acid ester to 1,1-dichloro-4-methyl-1,3-pentadiene to obtain a 2,2-dimethyl-3-(2',2'-dichlorovinyl) cyclopropanecarboxylic acid ester (J. Farkas et al, Collect. Czech. Chem. Commun., 24, 2230 (1959)). This process was not commercially profitable, either, partly because it provides only low yields and entails a danger of explosion and partly because the starting material 1,1-dichloro-4-methyl-1,3-pentadiene is not easy to be prepared.

We previously made an intensive study for the establishment of an industrial process for producing various substituted cyclopropane derivatives including 2,2-dimethyl-3-(2',2'-dihalogenovinyl) cyclopropanecarboxylic acids and/or their esters and ultimately discovered a method for producing cyclopropanecarboxylic acid esters of general formula (IV) which comprises treating an ester of said general formula (III) and/or an ester of general formula (V):

(wherein $R^1$, $R^2$, $R^3$, $R^4$, X and Y have the same meanings as respectively defined for general formula (III)) with a basic reagent. This treatment with a basic reagent can be carried out in the same manner as the treatment of said esters of general formula (III) with a basic reagent. The esters of general formula (III) and/or the esters of general formula (V) can be produced by the procedure shown below by way of reaction formulas

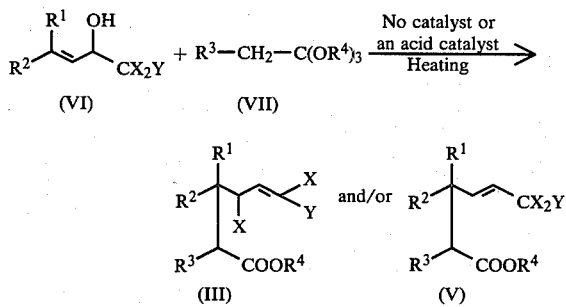

($R^1$, $R^2$, X and Y in general formula (VI) and $R^3$ and $R^4$ in general formula (VII) have the same meanings as respectively defined for general formulas (III) and (V)). Taking the production of 2,2-dimethyl-3-(2',2'-dichlorovinyl) cyclopropanecarboxylic acid ester as an example, isobutene and chloral are first reacted together to obtain 1,1,1-trichloro-4-methyl-4-penten-2-ol which, in turn, is isomerized to 1,1,1-trichloro-4-methyl-3-penten-2-ol. This 1,1,1-trichloro-4-methyl-3-penten-2-ol is reacted with an orthoacetic acid ester to obtain a 3,3-dimethyl-4,6,6-trichloro-5-hexenoic acid ester and/or a 3,3-dimethyl-6,6,6-trichloro-4-hexenoic acid ester, which is then treated with a basic reagent. By the above procedure can be obtained the desired 2,2-dimethyl-3-(2',2'-dichlorovinyl) cyclopropanecarboxylic acid ester. If a different orthocarboxylic acid ester is used in lieu of said orthoacetic acid ester, there is obtained a 1-substituted-2,2-dimethyl-3-(2',2'-dichlorovinyl) cyclopropanecarboxylic acid ester via the corresponding 2-substiuted-3,3-dimethyl-6,6,6-trichloro-4-hexenoic acid ester and/or 2-substituted-3,3-dimethyl-4,6,6-trichloro-5-hexenoic acid ester. For example, where an orthopropionic acid ester is employed, there is obtained a 1,2,2-trimethyl-3-(2',2'-dichlorovinyl) cyclopropanecarboxylic acid ester via a 2,3,3-trimethyl-6,6,6-trichloro-4-hexenoic acd ester and/or a 2,3,3-trimethyl-4,6,6-trichloro-5-hexenoic acid ester, Recently, the process has been proposed which comprises reacting 3-methyl-2-buten-1-ol with an orthoacetic acid ester to obtain a 3,3-dimethyl-4-pentenoic acid ester, adding a carbon tetrahalide to the last-mentioned ester to obtain a 3,3-dimethyl-4,6,6,6-tetrahalogenohexanoic acid ester and finally treating it with a basic reagent to produce a 2,2-dimethyl-3-(2',2'-dihalogenovinyl) cyclopropanecarboxylic acid ester (The 31st Fall Congress of Japanese Chemical Society, Kondo et al, A Collection of Manuscripts, 58 (1974). In the above process, too, by replacing said 3,3-dimethyl-4-pentenoic acid ester with another 3,3-dialkyl-4-pentenoic acid ester and said orthoacetic acid ester with a different orthocarboxylic acid ester, there can be obtained the corresponding 2-substituted-3,3-dialkyl-4,6,6,6-tetrahalogenohexanoic acid ester of general formula (VIII):

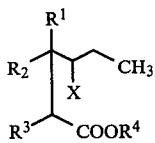
(VII)

(wherein $R^1$, $R^2$, $R^3$, $R^4$ and X have the same meanings as respectively defined for general formula (III)). This compound may be reacted with a basic reagent to obtain a cyclopropanecarboxylic acid ester of general formula (IV). This treatment with a basic reagent is carried out in the same manner as the treatment of ester (III) with a basic reagent.

As has been described hereinbefore, all the ester of general formula (III), the ester of general formula (V) and the ester of general formula (VIII), when treated with a basic reagent, undergo ring closure to yield substituted cylcopropane derivatives of the type represented by general formula (IV). Analysis of the by-products formed in the reactions revealed the presence of γ-lactone derivatives of general formula (I).

The reaction of an allylic alcohol of said general formula (VI) with an orthocarboxylic acid ester of general formula (VII) is carried out in the presence or absence of an acid catalyst and at temperatures in the range of 100° to 200° C., preferably, between 120° and 160° C. It has been found that, in this reaction, too, a γ-lactone derivative of general formula (I) is byproduced in a maximum yield of about 60 percent depending on the conditions of the reaction. As preferred examples of the acid catalyst to be thus employable, there may be mentioned formic acid, propionic acid, isobutyric acid, cyclohexanecarboxylic acid, adipic acid, benzoic acid, phenol, cresol, hydroquinone, p-toluenesulfonic acid, benzenesulfonic acid, sulfuric acid, hydrochloric acid, phsophoric acid, boric acid and so forth, althouth other similar acid catalysts may also be employed.

It has also been found that, in the treatment of ester (III), (V) or (VIII) with a basic reagent, said γ-lactone derivative (I) is produced in a large amount if water is present in the reaction system.

The ring-opening osterification ((I)→(III)) according to the present invention is very useful for the conversion of such a byproduct or concomitant product γ-lactone derivative to an ester of general formula (III) which may be easily caused to cyclize to a cyclopropanecarboxylic acid ester of the type represented by general formula (IV).

Therefore, the production economics of cyclopropanecarboxylic acid esters can be improved by modifying the production process of cyclopropanecarboxylic acids and incorporating the ring-opening esterification according to the present invention more positively in the overall production flow as will be described hereinafter.

After detailed investigations, it has been found that if the treatment of each of esters (III), (V) and (VIII) with a basic reagent is followed by treatment of the reaction mixture with an acid reagent, there are cases in which a free carboxylic acid of general formula (IX)

(IX)

(wherein $R^1$, $R^2$, $R^3$, X and Y have the same meanings as respectively defined for general formula (I)) is produced by the acidification of the salt of carboxylic acid (IX) which is present in the reaction system and/or by hydrolysis of at least a portion of an ester of the type represented by general formula (IV) which is also present in the reaction system. After all, as the cyclopropanecarboxylic acid derivative, there are obtained a carboxylic acid of general formula (IX) and/or an ester thereof (an ester of the type represented by general formula (IV). Moreover, it has also been found that γ-lactone derivatives of general formula (I) are produced in amounts exceeding those obtainable without said acid treatment, while entailing no substantial reduction in the yield of such cyclopropanecarboxylic acid derivatives. The output of such a γ-lactone derivative of general formula (I) varies according to the conditions used in the cyclization reaction of the starting material ester, especially the species of basic reagent used in that procedure. For example, even where an alkali metal alcoholate is used as the basic reagent, there is produced said γ-lactone derivative in a yield of about 4 to 10 percent, which is a relatively conservative figure, and where said basic reagent is an alkali metal hydroxide which is less costly and easier to handle in commerical runs, the yield may be as high as about 50 percent.

Thus, the process which, as described below, combines the above treatment for increasing the yield of γ-lactone derivatives without decreases in the yield of cyclopropanecarboxylic acid derivatives with the ring-opening esterification of such γ-lactone derivatives, including the step of recycling the ring-opening esterification product to the cyclization reaction stage, is conducive to an improved production economics of cyclopropanecarboxylic acid derivatives.

Thus, an ester selected from the class consisting of the esters of general formula (III), esters of general formula (V) and esters of general formula (VIII), or a mixture of such esters, is treated with a basic reagent and, then, with an acid reagent to obtain a cyclopropanecarboxylic acid derivative comprising a cyclopropanecarboxylic acid of general formula (IX) and/or an ester thereof (IV) and a γ-lactone derivative of general formula (I).

Then, (Process i) this γ-lactone derivative (I), together with said cyclopropanecarboxylic acid derivative, is treated with a hydrogen halide and an alcohol of general formula (II). From the reaction mixture is recovered a cyclopropanecarboxylic acid ester of general formula (IV), while the concomitantly produced ester of general formula (III) is treated with a basic reagent and, if necessary, further treated with an acid reagent to obtain an additional amount of cyclopropanecarboxylic acid derivative which is a cyclopropanecarboxylic acid of general formula (IX) and/or an ester thereof (IV).

In an alternative process (Process ii), said cyclopropanecarboxylic acid derivative is recovered independently of said γ-lactone derivative of general formula (I), while the latter γ-lactone derivative (I) is reacted with a hydrogen halide and an alcohol of general formula (II) and the resultant ester of general formula (III) is treated with a basic reagent and, if necessary, with an acid reagent to obtain an additional amount of cyclopropanecarboxylic acid derivative consisting of a cyclopropanecarboxylic acid of general formula (IX) and/or an ester thereof (IV). Accordingly, the overall yield of said cyclopropanecarboxylic acid derivative is markedly increased and, therefore, the economics of the production process is improved. In this connection, the treatment of an ester selected from the class consisting of the esters of general formula (III), esters of general formula (V) and esters of general formula (VIII) or a mixture of such esters with a basic reagent may be carried out in the same manner as the treatment with a basic reagent which has been described hereinbefore.

The product obtainable by the above treatment with a basic reagent contains a precursor (its structure remains yet to be elucidated) of γ-lactone derivative (I), in addition to said ester of cyclopropanecarboxylic acid (VII). Moreover, in certain cases, said product further contains a salt of cyclopropanecarboxylic acid (VII). If this treatment with a basic reagent is followed by treatment with an acid reagent in order to neutralize or acidify the reaction system, there are obtained the cyclopropanecarboxylic acid derivative consisting of cyclopropanecarboxylic acid (VII) and/or its ester and a γ-lactone derivative (I). As preferred examples of the acid reagent thus employable, there may be mentioned hydrogen chloride, hydrogen bromide, phosphoric acid, sulfuric acid, formic acid, acetic acid, monochloroacetic acid, phenol, p-toluenesulfonic acid and so forth, although other similar acid reagents may also be employed. The proportion of such acid reagent may be just enough to neutralize the reaction mixture following the treatment with a basic reagent. However, it is not objectionable to acidify the reaction mixture using a slight excess of acid reagent. While there are no particular limits to the temperature of this acid treatment, the treatment is preferably conducted at a temperature not exceeding 40° C. so as to inhibit hydrolysis of the ester of cyclopropanecarboxylic acid (VII) or other side reactions.

In the present invention, the aforementioned γ-lactone derivative (I) is reacted with a hydrogen halide and an alcohol (II) to obtain the corresponding ester of general formula (III). This reaction is effected: (a) by permitting a hydrogen halide and an alcohol to act upon the mixture of cyclopropanecarboxylic acid derivative and γ-lactone derivative (I) obtained by said treatment with an acid reagent or (b) by separating said cyclopropanecarboxylic acid derivative from γ-lactone derivative (I) and permitting a hydrogen halide and an alcohol to act upon the γ-lactone derivative (I) thus isolated. The order of charging the hydrogen halide and alcohol has already been described hereinbefore. Generally, it is desirable: (A) to introduce a hydrogen halide into the alcohol and, then, add said γ-lactone derivative (I) or said mixture of γ-lactone derivative (I) and cyclopropanecarboxylic acid derivative to the above-obtained alcohol solution or (B) to add the hydrogen halide to a system in which both said alcohol and said γ-lactone derivative (I) or said mixture of γ-lactone derivative (I) and cyclopropanecarboxylic acid derivative are present. While the alcohol is is preferably a lower alcohol such as methanol, ethanol, propanol, butanol or the like, other alcohols within the ambit of general formula (II) may be employed, if desired. The proportion of alcohol has already been mentioned, but where the system includes a cyclopropanecarboxylic acid (II), it is preferable to employ about 0.5 to 10 times the stoichiometric amount of alcohol necessary for the ring-opening esterification of γ-lactone derivative and the esterification of the cyclopropanecarboxylic acid. Other conditions of reaction have already been described hereinbefore.

After the above reaction, if there are residues of hydrogen halide and/or alcohol, these are separated and recovered, e.g. by distillation, followed by further distillation of the residue under reduced pressure. By this procedure is obtained, in the case of the above (Process ii), the ester of general formula (III) which is the product of reaction of γ-lactone derivative with hydrogen halide and alcohol, whereas in the case of (Process i), there is obtained the ester of general formula (III) together with the ester of cyclopropanecarboxylic acid (IX). The ester of general formula (III) and ester of cyclopropanecarboxylic acid (IX) thus obtained are the esters possessing the alcohol residue originating from the alcohol used in the ring-opening esterification of γ-lactone derivative (I) and/or the ester supplied to this reaction system, the composition thereof being variable according to such factors as the composition of the cyclopropanecarboxylic acid derivative fed to this reaction system and the species and amount of alcohol used in the reaction.

The ester of general formula (III) thus obtained from byproduct γ-lactone derivative (I) is treated with a basic reagent and, if necessary, further with an acid reagent, whereby an additional amount of cyclopropanecarboxylic acid derivative (cyclopropanecarboxylic acid (IX) and/or its ester) is obtained. These treatments with a basic reagent and with an acid reagent may be carried out in the same manner as the corresponding treatments of starting ester with such reagents which have been described hereinbefore.

Only for the purpose of assisting in the understanding of the above-mentioned (Process i) and (Process ii), a few working examples will be schematically described. In the following formulas, Me means a methyl group and Et means an ethyl group.

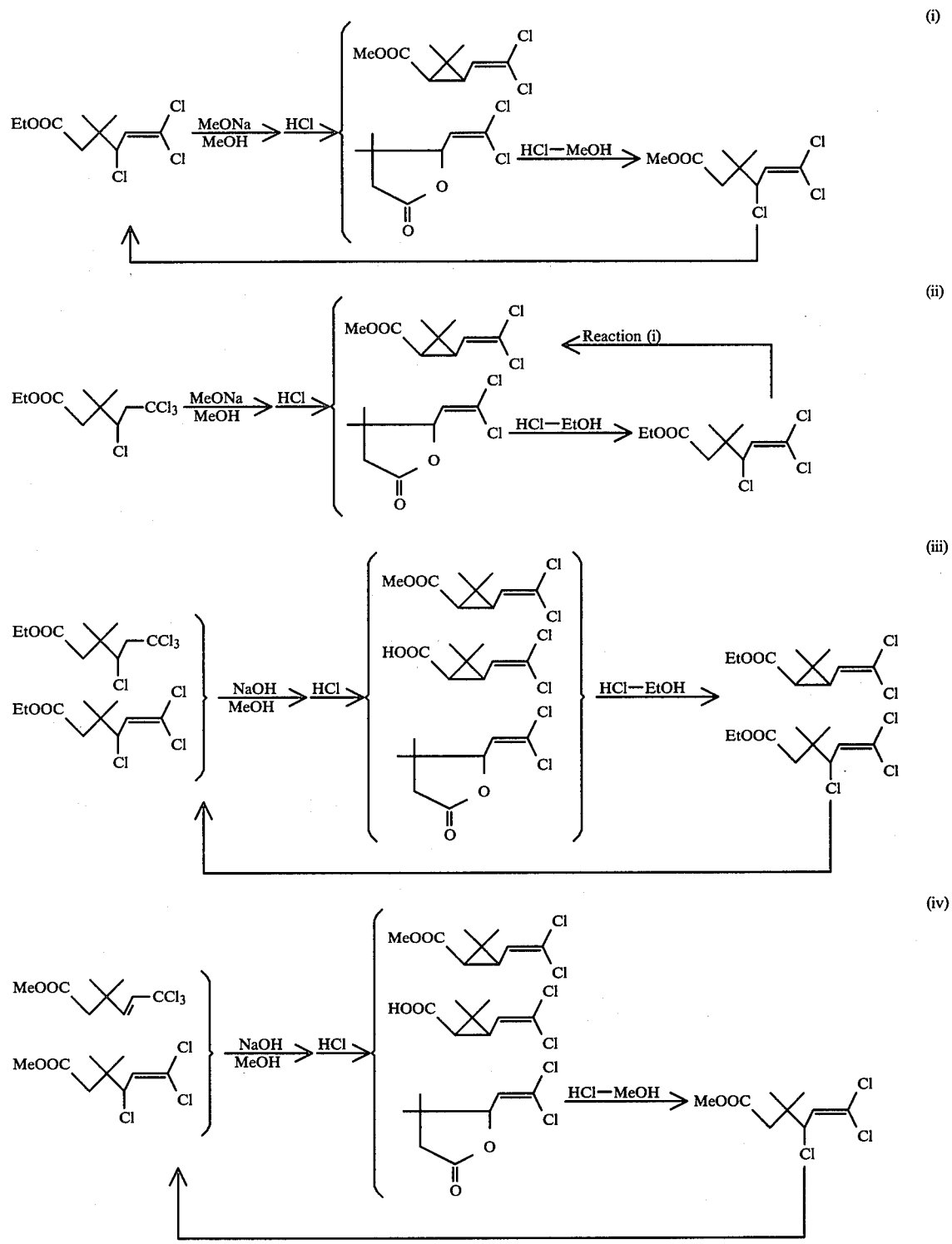

Particularly where, among said basic reagents, an alkali metal hydroxide is employed (in this case, the total yield of said cyclopropanecarboxylic acid derivative and γ-lactone derivative is maximal, whereas other byproducts are substantially absent), the γ-lactone derivative (I) may also be effectively utilized by the following procedure to obtain the cyclopropanecarboxylic acid ester (IV) in good yield.

Thus, an ester selected from the class consisting of the esters of general formula (III), esters of general formula (V) and esters of general formula (VIII) or a mixture of such esters is treated with an alkali metal hydroxide and, then, with an acid reagent to obtain a cyclopropanecarboxylic acid derivative consisting of cyclopropanecarboxylic acid (IX) and its ester (IV) and a γ-lactone derivative of general formula (I). Then, (Process iii) this cyclopropanecarboxylic acid derivative, together with said γ-lactone derivative, is heated with an alcohol (II) in the presence of an acid catalyst and, from the resultant reaction mixture, the cyclopropanecarboxylic acid ester of general formula (IV) is separated from the γ-lactone derivative of general formula (I) and recovered, whereas the γ-lactone derivative (I) is reacted with a hydrogen halide and an alcohol (II) to obtain an ester of general formula (III), which, in turn, is treated with an alkali metal hydroxide and, then, with an acid reagent. The thus-obtained mixture of a cyclopropanecarboxylic acid derivative consisting of a cyclopropanecarboxylic acid of general formula (IX) and an ester thereof (IV) and a γ-lactone derivative of general formula (I) is heated together with an alcohol (II) in the presence of an acid catalyst, followed by separation of an additional amount of cyclopropanecarboxylic acid ester (IV). The above treatment of an ester selected from the class consisting of the esters of general formula (III), esters of general formula (V) and esters of general formula (VIII) or a mixture of such esters with an alkali metal hydroxide may be carried out in the same manner as the treatment with a basic reagent which has already been described hereinbefore. The treatment with an acid reagent which follows this treatment with an alkali metal hydroxide may also be carried out in the same manner as the treatment with an acid reagent which has been described with reference to (Process i) and (Process ii).

In the above (Process iii), the cyclopropanecarboxylic acid derivative consisting of a cyclopropanecarboxylic acid of general formula (IX) and its ester of general formula (IV) and the γ-lactone derivative of general formula (I) are treated with an alcohol (II) under heating and in the presence of an acid catalyst. This treatment causes the carboxylic acid of general formula (IX) to undergo esterification with the alcohol used to yield the corresponding carboxylic acid ester in high yield. The carboxylic acid ester (IV) applied to this treatment stage, where the alcohol used in this treatment is an alcohol not corresponding to the alcohol residue of said ester, is converted to the carboxylic acid ester whose alcohol residue corresponds to the alcohol used in the treatment as said treatment causes a part or all of the supplied ester to undergo esterification. Preferred examples of the alcohol are lower alcohols such as methanol, ethanol, propanol, butanol, etc., although other alcohols within the ambit of general formula (II) may also be employed. The acid catalyst may be one of the acid catalysts which are normally used as catalysts for esterification reactions, particularly desirable catalysts including formic acid, propionic acid, isobutyric acid, cyclohexanecarboxylic acid, adipic acid, benzoic acid, phenol, cresol, hydroquinone, p-toluenesulfonic acid, benzenesulfonic acid, sulfuric acid, hydrochloric acid, phosphoric acid, boric acid and so forth. The amount of acid catalyst is desirably about 0.01 to 10 weight percent based on the weight of the cyclopropanecarboxylic acid derivative obtained upon treatment with an alkali metal hydroxide. It is to be understood that the γ-lactone derivative of general formula (I) is not modified at all in the above treatment. From the resultant mixture containing the ester (IV) of carboxylic acid (IX) and the γ-lactone derivative of general formula (I), the two compounds are independently separated. This separation may be easily accomplished by distillation.

In this (Process iii), the above byproduct γ-lactone derivative (I) is further reacted with a hydrogen halide and an alcohol (II) to obtain the corresponding ester of general formula (III). This reaction is carried out after the γ-lactone derivative (I) is separated from the above ester (IV) of cyclopropanecarboxylic acid (IX), by permitting a hydrogen halide and an alcohol (II) to act upon the γ-lactone derivative thus separated. Following this reaction, if there are residues of hydrogen halide and/or alcohol, these residues are separated by distillation and recovered. The distillation residue is further distilled under reduced pressure to obtain the ester of general formula (III).

The ester of general formula (III) obtained from the byproduct γ-lactone derivative (I) in the above manner is treated with an alkali metal hydroxide and, then, with an acid reagent to obtain a mixture of a cyclopropanecarboxylic acid derivative consisting of a cyclopropanecarboxylic acid of general formula (IX) and an ester thereof (IV) and a γ-lactone derivative (I). This mixture is heated together with an alcohol (II) in the presence of an acid catalyst and the cyclopropanecarboxylic acid ester (IV) is then separated and recovered. The above treatment with an alkali metal hydroxide, the treatment with an acid reagent and the treatment with an alcohol under heating in the presence of an acid catalyst may also be carried out in the same manners as the treatment of starting material ester with an alkali metal hydroxide, treatment with an acid reagent and subsequent treatment by heating with an alcohol in the presence of an acid catalyst, respectively, which have been described hereinbefore.

Only for the purpose of assisting in a better understanding of (Process iii), a few modes of embodiment will be schematically shown below. In the following formulas, Me, Et and TosOH stand for methyl, ethyl and p-toluenesulfonic acid, respectively.

(v) 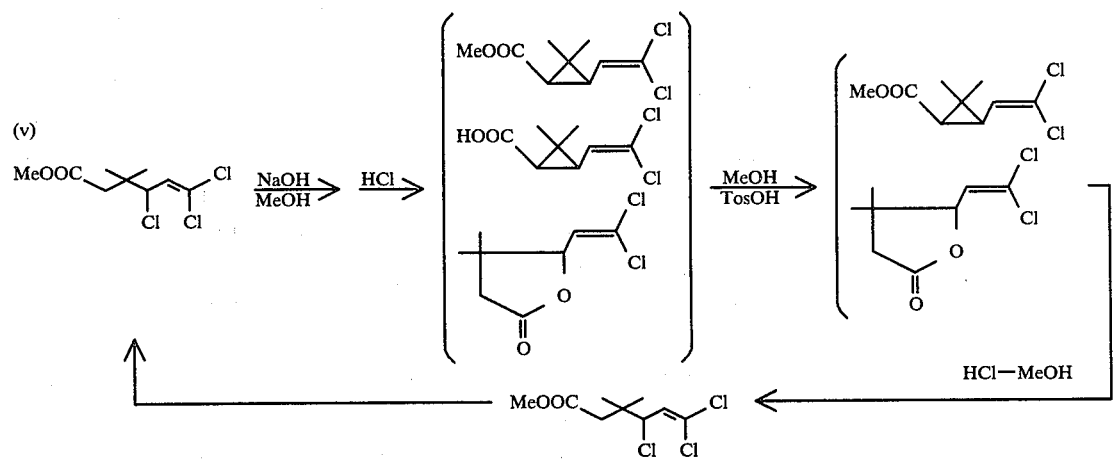
(vi) 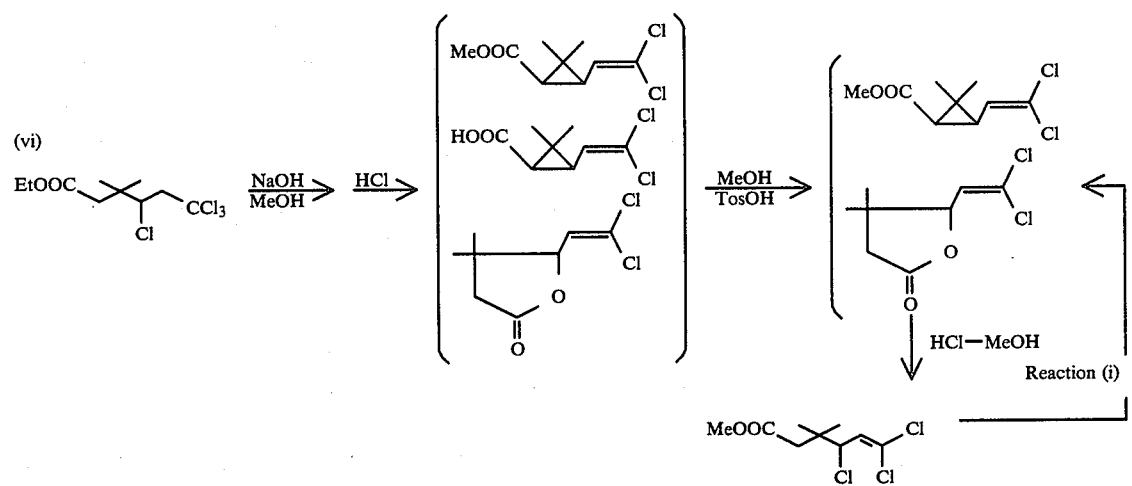
(vii) 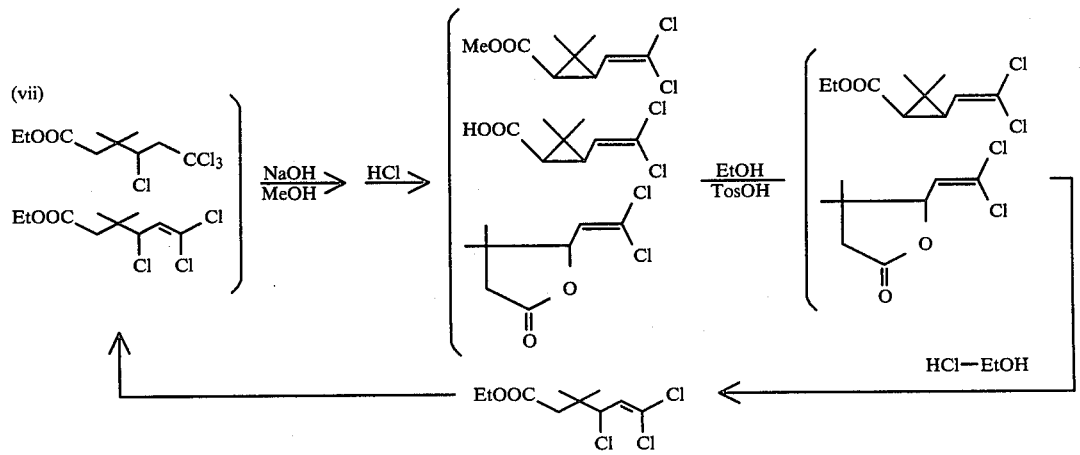

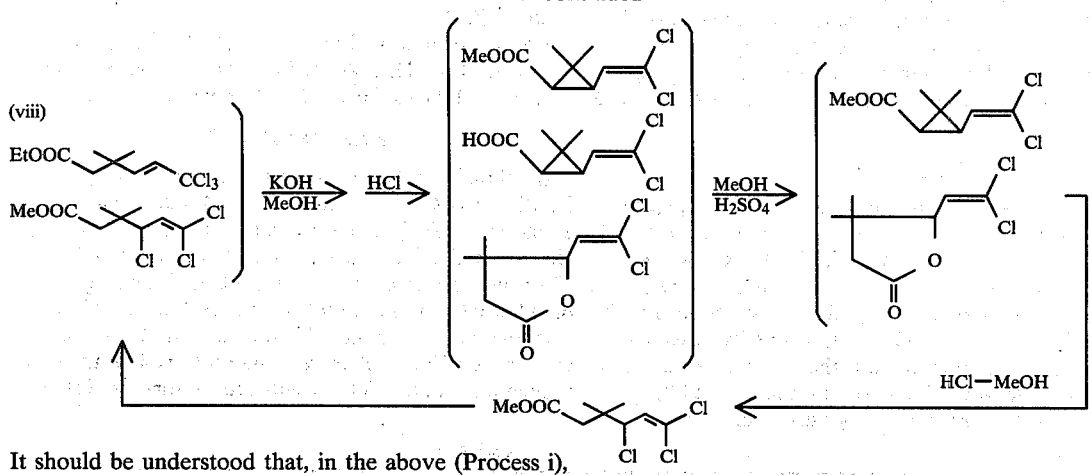

It should be understood that, in the above (Process i), instead of separating and recovering the cyclopropanecarboxylic acid ester (IV) from the reaction mixture following the treatment of a mixture of γ-lactone derivative (I) and cyclopropanecarboxylic acid derivative with hydrogen halide and alcohol (II), said reaction mixture may be directly subjected to said treatment with a basic reagent. Moreover, referring to the above (Process iii), instead of separating and recovering the cyclopropanecarboxylic acid ester (IV) from the reaction mixture following the treatment of a mixture of γ-lactone derivative and cyclopropanecarboxylic acid derivative by heating with alcohol (II) in the presence of an acid catalyst, said reaction mixture may be directly reacted with hydrogen halide and alcohol (II).

It should also be understood that the treatments according to (Process i), (Process ii) and (Process iii) may be carried out independently of the processing steps hereinbefore described but when the above (Process i), (Process ii) and (Process iii) are carried out in repetition or continuously, it is desirable to recycle the ester (III) obtained from the by-produced or concomitantly produced γ-lactone derivative (I) as a portion of starting material to the stage in which the treatment of starting ester with a basic reagent is performed. In this manner, the necessary initial amount of starting material ester can be considerably reduced. The foregoing method not only enables one to convert the byproduced or concomitantly produced γ-lactone derivatives to useful compounds and thereby to obtain the cyclopropanecarboxylic acid derivatives in good yield but also has the advantage that the restrictions on the conditions of said ring-closing reaction are considerably alleviated.

The following examples are further illustrative of the present invention. In these examples, all parts are by weight and, unless otherwise specified, all NMR data are those obtained in carbon tetrachloride with tetramethylsilane as the internal reference at room temperature and 60 MHz.

EXAMPLE 1

To 80 parts of a methanolic solution of hydrogen chloride (concentration of hydrogen chloride: about 47%) was added 100 parts of 3,3-dimethyl-4-(2′,2′-dichlorovinyl)-4-butanolide (in general formula (I), X, Y=Cl; $R^1$, $R^2$=CH$_3$; $R^3$=H) and the mixture was stirred at room temperature for 12 hours. The reaction mixture was directly distilled to recover the excess hydrogen chloride and methanol and further distilled under reduced pressure. By the above procedure was obtained 116 parts of methyl 3,3-dimethyl-4,6,6-trichloro-5-hexenoate (yield 94%), the properties of which are given below.

bp: 80°–82° C./0.3 mmHg
NMR spectrum (δ): 1.15 (s) 6H, 2.22 (d, J=14 Hz) 1H, 2.55 (d, J=15 Hz) 1H, 3.68 (s) 3H, 4.93 (d, J=11 Hz) 1 H, 6.10 (d, J=11 Hz) 1 H
IR spectrum (liquid film): 1615 cm$^{-1}$ (C=C), 1735 cm$^{-1}$ (CO)

EXAMPLE 2

To 100 parts of an ethanolic solution of hydrogen chloride (concentration of hydrogen chloride: about 45%) was added 100 parts of 3,3-dimethyl-4-(2′,2′-dichlorovinyl)-4-butanolide and the mixture was stirred at room temperature for 18 hours. Thereafter, the reaction mixture was treated in the same manner as Example 1. By this procedure was obtained 120 parts of ethyl 3,3-dimethyl-4,6,6-trichloro-5-hexenoate (yield 92%), the properties of which are given below.

bp: 91°–92° C./0.4 mmHg
IR spectrum (liquid film): 1610 cm$^{-1}$ (C=C), 1730 cm$^{-1}$ (CO)
NMR spectrum (100 MHz) δ: 1.08 (s) 6H, 1.20 (t, J=7 Hz) 3H, 2.14 (d, J=14 Hz) 1H, 2.42 (d, J=14 Hz) 1H, 4.01 (q, J=7 Hz) 2 H, 4.83 (d, J=11 Hz) 1H, 5.95 (d, J=11 Hz) 1H
Elemental analysis (Calcd. values in parentheses): C, 43.77(43.90)%; H, 5.47 (5.53)%

EXAMPLE 3

Under cooling with ice, hyrogen chloride gas was bubbled into a mixture of 50 parts of 3,3-dimethyl-4-(2′,2′-dichlorovinyl)-4-butanolide and 100 parts of methanol. After it was confirmed by gas chromatography that the reaction had gone to completion, the reaction mixture was treated in the same manner as Example 1. By the above procedure was obtained 56 parts of methyl 3,3-dimethyl-4,6,6-trichloro-5-hexenoate (yield 90%). This product was shown to have properties identical with those of the ester obtained in Example 1.

EXAMPLE 4

To 30 parts of methanol saturated with hydrogen chloride gas (concentration of hydrogen chloride: about 50%) was added 41.8 parts of 3,3-dimethyl-4-(2′,2′-dichlorovinyl)-4-butanolide, followed by heating in a closed tubular reactor at 70°–80° C. for 3 hours. The reaction mixture was then treated in the same manner as Example 1. By the above procedure was obtained 49.8 parts of methyl 3,3-dimethyl-4,6,6-trichloro-5-hexenoate (yield 96%). This product was found to have properties identical with those of the product according to Example 1.

EXAMPLE 5

The procedure of Example 2 was repeated except that 107 parts of 2,3,3-trimethyl-4-(2',2'-dichlorovinyl)-4-butanolide (in general formula (I), X, Y=Cl; $R^1$, $R^2$, $R^3$=$CH_3$) was used in lieu of 3,3-dimethyl-4-(2',2'-dichlorovinyl)-4-butanolide. By the above procedure was obtained 32 parts of ethyl 2,3,3-trimethyl-4,6,6-trichloro-5-hexenoate which had the properties given below. The yield was 92% based on the reacted 2,3,3-trimethyl-4-(2',2'-dichlorovinyl)-4-butanolide.

bp: 104°–106° C./0.4 mmHg
IR spectrum (liquid film): 1610 cm$^{-1}$ (C=C), 1730 cm$^{-1}$ (CO) NMR spectrum (100 MHz)δ: 1.20 (t, j=9 Hz), 0.9–1.3, 12 H; 2.4–2.7 (m) 1H; 4.01 (q, J=7 Hz), 4.03 (q, J=7 Hz) 2H; 4.63 (d, J=11 Hz), 4.78 (d, J=11 Hz) 1H; 5.96 (d, J=11 Hz), 5.97 (d, J=11 Hz) 1H
Elemental analysis (Calcd. values in parentheses): C, 46.20 (45.94)% H; 6.02 (5.96)%

EXAMPLE 6

Under cooling with ice, hydrogen bromide gas was bubbled into a mixture of 29.8 parts of 3,3-dimethyl-4-(2',2'-dibromovinyl)-4-butanolide and 100 parts of ethanol. After it was confirmed by gas chromatography that the reaction had gone to completion, the reaction mixture was treated in the same manner as Example 1. By the above procedure was obtained 33.3 parts of ethyl 3,3-dimethyl-4,6,6-tribromo-5-hexenoate (yield 82%) which was shown to have the following properties.

IR spectrum (liquid film): 1600 cm$^{-1}$ (C=C), 1730 cm$^{-1}$ (CO)
NMR spectrum δ: 1.12 (s) 6H, 1.22 (t, J=7 Hz) 3H, 2.17 (d=15 Hz) 1 H, 2.49 (d, J=15 Hz) 1H, 4.08 (q, J=7 Hz) 2H, 4.93 (d, J=11 Hz) 1H, 6.66 (d, J=11 Hz) 1H

EXAMPLES 7–9

In 30 parts of diethyl ether was dissolved 4.2 parts of 3,3-dimethyl-4-(2',2'-dichlorovinyl)-4-butanolide and, as shown in Table 1, n-octyl alcohol, 3-phenoxybenzyl alcohol or allethrolone was added to the above solution. Then, at room temperature, hydrogen chloride gas was bubbled into the solution for 2 hours. The, low-boiling fractions were distilled off and the residue was chromatographed on a silica gel column to isolate the contemplated product. The results are set forth in Table 1.

TABLE 1

| Example | Alcohol, parts | | Product, parts (% yield) | NMR spectrum of product, δ |
|---|---|---|---|---|
| 7 | n-Octyl alcohol [n-C$_8$H$_{17}$OH] 13 | 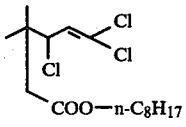 | 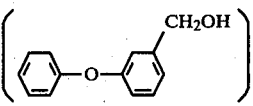  2.5 (35) | 0.85 (t, J = 6Hz) 3H, 1.08 (s) 6H, 1.29(bs) 12H, 2.16 (d, J = 15Hz) 1H, 2.49 (d, J = 15Hz) 1H, 4.02(d, J = 6Hz) 2H, 4.90(d, J = 11Hz) 1H, 6.07(d, J = 11Hz) 1H |
| 8 | 3-Phenoxybenzyl alcohol 20 | 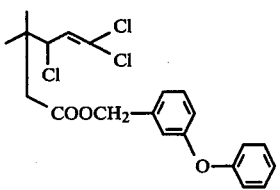 | 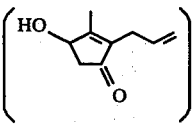  1.1 (13) | 1.03 (s) 6H, 2.18 (d, J = 15Hz) 1H, 2.52 (d, J = 15Hz) 1H, 4.87 (d, J = 11Hz) 1H, 5.02 (s) 2H, 6.02 (d, J = 11Hz) 1H, 6.80–7.50 (m) 9H |
| 9 | Allethrolone 15 | | 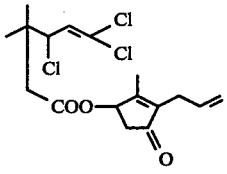  0.8 (10) | 1.12 (s) 6H, 1.98 (bs) 3H, 2.13–3.08 (m) 6H, 4.72–6.50 (m) 6H |

EXAMPLE 10

In 30 parts of methanol was dissolved 6.0 parts of sodium hydroxide. Separately, a mixture of 26.0 parts of methyl 3,3-dimethyl-4,6,6-trichloro-5-hexenoate and 13 parts of methanol was prepared. The methanolic solution of sodium hydroxide was added dropwise to the latter mixture under reflux over a period of 30 minutes, followed by stirring at that temperature for 30 minutes. Thereafter, the reaction mixture was allowed to cool and neutralized with concentrated hydrochloric acid. The methanol was distilled off under reduced pressure to recover a mixture of oily product and solid sodium chloride. The solid was dissolved by the addition of water, followed by extraction wih diethyl ether. The ether layer was dried over anhydrous magnesium sulfate and the ether was distilled off. By the above procedure was obtained 22.5 parts of a mixture of 2,2-dimethyl-3-(2',2'-dichlorovinyl)-cyclopropanecarboxylic acid, methyl 2,2-dimethyl-3-(2',2'-dichlorovinyl) cyclopropanecarboxylate and 3,3-dimethyl-4-(2',2'-dichlorovinyl)-4-butanolide. To this mixture was added 25 parts of methanol in which hydrogen chloride gas had been absorbed (concentration of hydrogen chloride: about 50%), followed by stirring at room temperature overnight. Then, the excess hydrogen chloride and methanol were distilled off under reduced pressure, whereupon 24.4 parts of oily product was obtained as the residue. Gas chromatographic analysis revealed that this product was a mixture of 15.9 parts of methyl 2,2-dimethyl-3-(2',2'-dichlorovinyl) cyclopropanecarboxylate (yield 71%, cis/trans ratio=24:76) and 7.0 parts of methyl 3,3-dimethyl-4,6,6-trichloro-5-hexenoate (27% based on starting material). This mixture was then distilled under reduced pressure to recover 14.2 parts of methyl 2,2-dimethyl-3-(2',2'-dichlorovinyl) cyclopropanecarboxylate (bp: 67°–69° C./0.2 mmHg, NMR (δ):1.12–1.25 (m) 6H, 1.42–2.25 (m) 2H, 3.60 (s) 3H, 5.57 (d, J=8.5 Hz), 6.23 (d, J=8.5 Hz) 1H) and 5.9 parts of methyl 3,3-dimethyl-4,6,6-trichloro-5-hexenoate (bp: 80°–82° C./0.3 mmHg; NMR (δ): 1.15 (s) 6H, 2.22 (d, J=15 Hz) 1H, 2.55 (d, J=15 Hz) 1H, 3.68 (s) 3H, 4,93 (d, J=11 Hz) 1H, 6.10 (d, J=11 Hz) 1 H; IR (liquid film) 1615 cm$^{-1}$ (C=C), 1735 cm$^{-1}$ (CO)).

To 5.9 parts of the above methyl 3,3-dimethyl-4,6,6-trichloro-5-hexenoate was added a sufficient amount of fresh methyl 3,3-dimethyl-4,6,6-trichloro-5-hexenoate to make a total of 26.0 parts and exactly the same procedure as above was repeated. After distillation, there were obtained 14.0 parts of methyl 2,2-dimethyl-3-(2',2'-dichlorovinyl) cyclopropanecarboxylate and 6.1 parts of methyl 3,3-dimethyl-4,6,6-trichloro b 5-hexenoate. By repeating this recycle of byproduct methyl 3,3-dimethyl-4,6,6-trichloro-5-hexenoate to fresh starting material, there was obtained methyl 2,2-dimethyl-3-(2',2'-dichlorovinyl) cyclopropanecarboxylate in a yield of 97% based on starting methyl 3,3-dimethyl-4,6,6-trichloro-5-hexenoate.

EXAMPLE 11

In 100 parts of methanol was dissolved 5.5 parts of sodium metal and, while the reaction temperature was maintained at 40°–50° C., 51.9 parts of methyl 3,3-dimethyl-4,6,6-trichloro-5-hexonoate was added dropwise to the above solution over a period of about an hour. The mixture was then stirred at room temperature for about 1.5 hours. The reaction mixture was allowed to cool and neutralized with a methanolic solution of hydrogen chloride. The methanol was then distilled off under reduced pressure. By the above procedure was obtained a mixture of oily product and solid sodium chloride. The solid was dissolved by the addition of water, followed by extraction with diethyl ether. The ether layer was dried over anhydrous magnesium sulfate and the ether was then distilled off. The procedure provided 45.1 parts of an oily product. This product was subjected to distillation under reduced pressure. The distillation procedure yielded, as a first cut, 40.2 parts of methyl 2,2-dimethyl-3-(2',2'-dichlorovinyl)cyclopropanecarboxylate (yield 90%; cis/trans ratio=25:75; bp: 67°–69° C. /0.2 mmHg) and, then, 2.1 parts of 3,3-dimethyl-4-(2',2'-dichlorovinyl)-4-butanolide (yield 5% bp: 94°–97° C./0.4 mmHg; NMR (δ):1.01 (s) 3H, 1.19 (s) 3H, 2.13 (d, J=17 Hz) 1H, 2.43 (d,J=17 Hz) 1H, 4.78 (d, J=9 Hz) 1H, 5.95 (d, J=9 Hz) 1H; IR (liquid film): 1620 cm$^{-1}$ (C=C), 1785 cm$^{-1}$ (CO)). To 2.1 parts of the latter distillate 3,3-dimethyl-4-(2',2'-dichlorovinyl)-4-butanolide was added 2 parts of a methanolic solution of hydrogen chloride (concentration of hydrogen chloride: about 50%) and the mixture was stirred at room temperature overnight. The excess hydrogen chloride and methanol were distilled off under reduced pressure and the resultant residue was distilled under reduced pressure. The procedure provided 2.5 parts of methyl 3,3-dimethyl-4,6,6-trichloro-5-hexenoate (yield 96% based on 3,3-dimethyl-4-(2',2'-dichlorovinyl)-4-butanolide; bp: 80°–82° C./0.3 mmHg).

To the methyl 3,3-dimethyl-4,6,6-trichloro-5-hexenoate thus obtained (2.5 parts) was added a sufficient amount of fresh methyl 3,3-dimethyl-4,6,6-trichloro-5-hexenoate to make a total of 51.9 parts and the mixture was subjected to exactly the same procedure as described above. After the distillation stage, there was obtained 40.6 parts of methyl 2,2-dimethyl-3-(2',2'-dichlorovinyl) cyclopropanecarboxylate. The 3,3-dimethyl-4-(2',2'-dichlorovinyl)-4-butanolide (2.0 parts) concomitantly produced in the above procedure was treated with a methanolic solution of hydrogen chloride. By the above procedure was obtained 2.5 parts of methyl 3,3-dimethyl-4,6,6-trichloro-5-hexenoate.

Thus, by repeating the procedure of converting the 3,3-dimethyl-4-(2',2'-dichlorovinyl)-4-butanolide to methyl 3,3-dimethyl-4,6,6-trichloro-5-hexenoate and recycling the latter compound as an additional amount of starting material, methyl 2,2-dimethyl-3-(2',2'-dichlorovinyl) cyclopropanecarboxylate was obtained in an overall yield of 95% (based on methyl 3,3-dimethyl-4,6,6-trichloro-5-hexenoate).

EXAMPLE 12

In 100 parts of methanol was dissolved 16.0 parts of sodium hydroxide. Separately, a mixture of 31.0 parts of ethyl 3,3-dimethyl-4,6,6,6-tetrachlorohexanoate and 30 parts of methanol was prepared. The above methanolic solution of sodium hydroxide was added dropwise under reflux to said mixture over a period of 30 minutes, followed by stirring at that temperature for 30 minutes. The reaction mixture was allowed to cool and neutralized with concentrated hydrochloric acid. The methanol was then distilled off under reduced pressure to recover a mixture of oily product and solid sodium chloride. The solid was dissolved by the addition of water, followed by extraction with diethyl ether. The ether layer was dried over anhydrous magnesium sulfate and the ether was distilled off. By the above procedure was obtained 21.4 parts of a mixture of methyl 2,2-dimethyl-3-(2',2'-dichlorovinyl) cyclopropanecarboxylate, 2,2-dimethyl-3-(2',2'-dichlorovinyl) cyclopropanecarboxylic acid and 3,3-dimethyl-4-(2',2'-dichlorovinyl)-4-butanolide.

To the above mixture was added 20 parts of a methanolic solution of hydrogen chloride gas (concentration of hydrogen chloride: about 50%), followed by stirring at room temperature overnight. Thereafter, the excess hydrogen chloride and methanol were distilled off under reduced pressure, whereupon 22.5 parts of oily product was obtained as a residue. Gas chromatographic analysis showed that this residue was a mixture of 9.4 parts of methyl 2,2-dimethyl-3-(2',2'-dichlorovinyl) cyclopropanecarboxylate (yield 42% cis/trans ratio=25:75) and 12.7 parts of methyl 3,3-dimethyl-4,6,6-trichloro-5-hexenoate (yield 49%).

This mixture was subjected to distillation under reduced pressure to separate 8.5 parts of methyl 2,2-dimethyl-3-(2',2'-dichlorovinyl) cyclopropanecarboxylate (bp: 67°–69° C./0.2 mmHg) and 11.8 parts of methyl 3,3-dimethyl-4,6,6-trichloro-5-hexenoate (bp: 80°–82° C./0.3 mmHg). The latter compound methyl 3,3-dimethyl-4,6,6-trichloro-5-hexenoate was then treated in exactly the same manner as Example 10. In this manner, methyl 2,2-dimethyl-3-(2',2'-dichlorovinyl) cyclopropanecarboxylate was obtained in a yield of 97%.

EXAMPLE 13

In 200 parts of ethanol was dissolved 10.4 parts of sodium metal and, at a constant temperature of 55°–60° C., 46.6 parts of ethyl 3,3-dimethyl-4,6,6,6-tetrachlorohexanoate was added to the above solution dropwise over a period of 1 hour. The mixture was then stirred at the same temperature for 2 hours. The reaction mixture was then allowed to cool and neutralized with an ethanolic solution of hydrogen chloride. The ethanol was distilled off under reduced pressure to obtain a mixture of oily product and solid sodium chloride. The solid was dissolved by the addition of water, followed by extraction with diethyl ether. The ether layer was dried over anhydrous magnesium sulfate and the ether was distilled off. By the above procedure was obtained 36.5 parts of oily product.

This product was further subjected to distillation under reduced pressure to separate 25.5 parts of ethyl 2,2-dimethyl-3-(2',2'-dichlorovinyl) cyclopropanecarboxylate (yield 72%, cis/trans ratio=29:71, bp: 72°–74° C./0.4 mmHg; NMR (100 MHz)δ:1.12–1.40 (m) 9H; 1.45–2.30 (m) 2H; 4.12 (q, J=7 Hz) 2H; 5.63 (d, J=8 Hz), 6.29 (d, J=8 Hz) 1H) and 3.0 parts of 3,3-dimethyl-4-(2',2'-dichlorovinyl)-4-butanolide (yield 10%, bp: 94°–97° C./0.4 mmHg).

To this latter compound 3,3-dimethyl-4-(2',2'-dichlorovinyl)-4-butanolide (3.0 parts) was added 3.5 parts of an ethanolic solution of hydrogen chloride (concentration of hydrogen chloride: about 45%) and the mixture was stirred at room temperature overnight. Then, the excess hydrogen chloride and ethanol were distilled off under reduced pressure and the residue was further distilled under reduced pressure. By this procedure was obtained 3.6 parts of ethyl 3,3-dimethyl-4,6,6-trichloro-5-hexanoate (yield 92% based on 3,3-dimethyl-4-(2',2'-dichlorovinyl)-4-butanolide; bp: 91°–92° C./0.4 mmHg; NMR (100 MHz) : 1.08(s)6H, 1.20 (t,J=7 Hz)3H, 2.14(d,J=14 Hz)1H, 2.42(d,J=14 Hz)1H, 4.01(q,J=7 Hz) 2H, 4.83 (d, J=11 Hz) 1H, 5.95 (d, J=11 Hz) 1H).

The ethyl 3,3-dimethyl-4,6,6-trichloro-5-hexenote (3.6 parts) obtained as above was added to 42.4 parts of starting material ethyl 3,3-dimethyl-4,6,6,6-tetrachlorohexanoate and the resultant mixture (mole ratio=1:10) was subjected to exactly the same procedure as described above. Following the distillation stage, there was obtained 25.7 parts of ethyl 2,2-dimethyl-3-(2',2'-dichlorovinyl) cyclopropanecarboxylate (yield 72%; cis/trans ratio=29:71; bp: 72°–75° C./0.4 mmHg). The 3,3-dimethyl-4-(2,2-dichlorovinyl)-4-butanolide concomitantly produced in the above procedure was treated with hydrogen chloride and ethanol, whereby 3.4 parts of ethyl 3,3-dimethyl-4,6,6-trichloro-5-hexanoate was obtained. By repeating the procedure of converting the byproduct 3,3-dimethyl-4-(2',2'-dichlorovinyl)-4-butanolide to ethyl 3,3-dimethyl-4,6,6-trichloro-5-hexenoate and recycling the latter compound as starting material, there was obtained ethyl 2,2-dimethyl-3-(2',2'-dichlorovinyl) cyclopropanecarboxylate in an overall yield of 78%.

EXAMPLE 14

The procedure of Example 10 was repeated except that a mixture of 14.8 parts of methyl 3,3-dimethyl-4,6,6,6-tetrachlorohexanoate and 12.9 parts of methyl 3,3-dimethyl-4,6,6-trichloro-5-hexenoate (mole ratio=1:1) was used in lieu of methyl 3,3-dimethyl-4,6,6-trichloro-5-hexenoate. By the above procedure was obtained 23.0 parts of a mixture of 2,2-dimethyl-3-(2',2'-dichlorovinyl) cyclopropanecarboxylic acid, methyl 2,2-dimethyl-3-(2',2'-dichlorovinyl) cyclopropanecarboxylate and 3,3-dimethyl-4-(2',2'-dichlorovinyl)-4-butanolide. This mixture was treated with a methanolic solution of hydrogen chloride (concentration of hydrogen chloride: about 50%) to obtain 23.8 parts of oily product. Gas chromatographic analysis showed that this product was a mixture of 13.8 parts of methyl 2,2-dimethyl-3-(2',2'-dichlorovinyl) cyclopropanecarboxylate (yield 62% based on starting material; cis/trans ratio=25:75) and 8.8 parts of methyl 3,3-dimethyl-4,6,6-trichloro-5-hexenoate (34% based on starting mixture). This mixture was then subjected to distillation under reduced pressure to obtain 12.5 parts of contemplated compound methyl 2,2-dimethyl-3-(2',2'-dichlorovinyl)-cyclopropanecarboxylate, followed by recovery of 8.0 parts of methyl 3,3-dimethyl-4,6,6-trichloro-5-hexenoate.

To the above methyl 3,3-dimethyl-4,6,6-trichloro-5-hexenoate (8.0 parts) was added 14.8 parts of methyl 3,3-dimethyl-4,6,6,6-tetrachlorohexenoate, together with 4.9 parts of methyl 3,3-dimethyl-4,6,6-trichloro-5-hexenoate to make a total of 27.7 parts and the mixture was subjected to exactly the same procedure as described above. Following the distillation stage, 12.8 parts of methyl 2,2-dimethyl-3-(2',2'-dichlorovinyl) cyclopropanecarboxylate and 8.2 parts of methyl 3,3-dimethyl-4,6,6-trichloro-5-hexenoate were obtained. By repeating the procedure of recycling the methyl 3,3-dimethyl-4,6,6-trichloro-5-hexenoate thus concomitantly produced as a starting material, there was obtained methyl 2,2-dimethyl-3-(2',2'-dichlorovinyl) cyclopropanecarboxylate in an overall yield of 94%.

EXAMPLE 15

The procedure of Example 11 was repeated except that a mixture of 26.0 parts of methyl 3,3-dimethyl-4,6,6-trichloro-5-hexenoate and 26.0 parts of methyl 3,3-dimethyl-6,6,6-trichloro-4-hexenoate (mole ratio=1:1) was used in lieu of methyl 3,3-dimethyl-4,6,6-trichloro-5-hexenoate to obtain 37.9 parts of methyl 2,2-dimethyl-3-(2',2'-dichlorovinyl) cyclopropanecarboxylate (yield 85% based on starting material; cis/-trans ratio=29:71) and 4.6 parts of 3,3-dimethyl-4-(2',2'-dichlorovinyl)-4-butanolide (yield 11% based on starting material). The latter compound 3,3-dimethyl-4-(2',2'-dichlorovinyl)-4-butanolide (4.6 parts) was treated with 5.0 parts of a methanolic solution of hydrogen chloride (concentration of hydrogen chloride: about 50%) to obtain 5.5 parts of methyl 3,3-dimethyl-4,6,6-trichloro-5-hexenoate (yield 96% based on 3,3-dimethyl-4-(2',2'-dichlorovinyl)-4-butanolide).

To this methyl 3,3-dimethyl-4,6,6-trichloro-5-hexenoate (5.5 parts) was added 26.0 parts of methyl 3,3-dimethyl-6,6,6-trichloro-4-hexenoate together with 20.5 parts of methyl 3,3-dimethyl-4,6,6-trichloro-5-hexenoate to make a total of 52.0 parts and the mixture was subjected to exactly the same procedure as above. Following the distillation stage, there was obtained 36.8 parts of methyl 2,2-dimethyl-3-(2',2'-dichlorovinyl) cyclopropanecarboxylate along with 5.8 parts of methyl 3,3-dimethyl-4,6,6-trichloro-5-hexenoate. By repeating the procedure of converting the 3,3-dimethyl-4-(2',2'-dichlorovinyl)-4-butanolide thus concomitantly produced to methyl 3,3-dimethyl-4,6,6-trichloro-5-hexenoate and recycling the latter as a starting material, there was obtained methyl 2,2-dimethyl-3-(2',2'-dichlorovinyl) cyclopropanecarboxylate in an overall yield of 95%.

EXAMPLE 16

In 80 parts of methanol was dissolved 12.0 parts of sodium hydroxide and, at the reflux temperature of methanol, 51.9 parts of methyl 3,3-dimethyl-4,6,6-trichloro-5-hexenoate was added dropwise to the above solution over a period of 30 minutes, followed by stirring the mixture at that temperature for 30 minutes. Then, about 50 parts of water was added and, after refluxing for about 30 minutes, the reaction mixture was allowed to cool and neutralized with concentrated hydrochloric acid. The methanol was distilled off under reduced pressure and the residue was extracted with diethyl ether. The ether layer was dried and the ether was distilled off, whereupon 42.2 parts of a mixture of 2,2-dimethyl-3-(2',2'-dichlorovinyl) cyclopropanecarboxylic acid and 3,3-dimethyl-4-(2',2'-dichloroviyl)-4-butanolide. This mixture was further distilled under reduced pressure to separate 10.4 parts of 3,3-dimethyl-4-(2',2'-dichlorovinyl)-4-butanolide (yield 25%; bp: 86°–91° C./0.2 mmHg) and 22.3 parts of 2,2-dimethyl-3-(2',2'-dichlorovinyl) cyclopropanecarboxylic acid (yield 53%; bp: 105°–108° C./0.2 mmHg). Then, 10.4 parts of the former product 3,3-dimethyl-4-(2',2'-dichlorovinyl)-4-butanolide was dissolved in 70 parts of methanol and, under cooling with ice, hydrogen chloride gas was bubbled into the solution for about 1.5 hours. Thereafter, the excess hydrogen chloride and methanol were distilled off under reduced pressure and the residue was further subjected to distillation under reduced pressure. By this procedure was obtained 12.1 parts of methyl 3,3-dimethyl-4,6,6-trichloro-5-hexenoate (yield 23% based on starting material).

The methyl 3,3-dimethyl-4,6,6-trichloro-5-hexenoate obtained as above was added to a fresh charge of methyl 3,3-dimethyl-4,6,6-trichloro-5-hexenoate and the starting material mixture was subjected to exactly the same procedure as described above to produce 2,2-dimethyl-3-(2',2'-dichlorovinyl) cyclopropanecarboxylic acid. By repeating the procedure of converting the 3,3-dimethyl-4-(2',2'-dichlorovinyl)-4-butanolide concomitantly obtained to methyl 3,3-dimethyl-4,6,6-trichloro-5-hexenoate and recycling and adding the latter to a fresh charge of starting material, there was obtained 2,2-dimethyl-3-(2',2'-dichlorovinyl) cyclopropanecarboxylic acid in an overall yield of 70% based on the methyl 3,3-dimethyl-4,6,6-trichloro-5-hexenoate employed.

EXAMPLE 17

In 50 parts of ethanol was dissolved 2.8 parts of sodium metal. Separately, a mixture of 28.8 parts of ethyl 2,3,3-trimethyl-4,6,6-trichloro-5-hexenoate and 20 parts of ethanol was prepared. The ethanolic solution of sodium metal was then added dropwise to this mixture at a constant temperature of 50°–60° C. over a period of 1 hour, followed by stirring at that temperature for 2 hours. Thereafter, the reaction mixture was neutralized and extracted with ether as in Example 11. By this procedure was obtained 25.8 parts of oily product. Column chromatography was carried out on this product (silica gel; elute=n-hexane-benzene (1:1)) to recover 20.0 parts of ethyl 1,2,2-trimethyl-3-(2',2'-dichlorovinyl) cyclopropanecarboxylate (yield 80%; NMR, δ: 1.04 (s), 1.13 (s), 1.18 (s), 1.23 (t, J=7 Hz) 12 H; 2.25 (d, J=8 Hz) 1 H; 4.08 (q, J=7 Hz) 2 H; 5.57 (d, J=8 Hz), 6.30 (d, J=8 Hz) 1 H) and 2.9 parts of 2,3,3-trimethyl-4-(2',2'-dichlorovinyl)-4-butanolide (yield 13%; NMR, δ: 0.78–1.17 (m) 9 H; 2.07–2.53 (m) 1 H; 4.71 (d, J=9 Hz), 4.74 (d, J=9 Hz) 1 H; 5.93 (d, J=9 Hz), 5.99 (d, J=9 Hz) 1H; m p: 58° C.

Then, by a procedure similar to that described in Example 13 the latter product 2,3,3-trimethyl-4-(2',2'-dichlorovinyl)-4-butanolide (2.9 parts) was treated with 8 parts of an ethanolic solution of hydrogen chloride (concentration of hydrogen chloride: about 45%) to obtain 3.4 parts of ethyl 2,3,3-trimethyl-4,6,6-trichloro-5-hexenoate (b p: 104°–106° C./0.4 mmHg; NMR (100 MHz)δ:1.20 (t, J=9 Hz), 0.9–1.3, 12 H; 2.4–2.7 (m) 1 H; 4.01 (q, J=7 Hz), 4.03 (q, J=7 Hz) 2 H; 4.63 (d, J=11 Hz), 4.78 (d, J=11 Hz) 1 H; 5.96 (d, J=11 Hz), 5.97 (d, J=11 Hz) 1 H; IR (liquid film): 1610 cm⁻¹ (C=O), 1730 cm⁻¹ (CO)). This compound was recycled and added to a fresh charge of starting material ethyl 2,3,3-trimethyl-4,6,6-trichloro-5-hexenoate and the mixture was subjected to exactly the same procedure as described above to obtain ethyl 1,2,2-trimethyl-3-(2',2'-dichlorovinyl)cyclopropanecarboxylate. By repeating the procedure of converting the 2,3,3-trimethyl-4-(2',2'-dichlorovinyl)-4-butanolide concomitantly obtained to ethyl 2,3,3-trimethyl-4,6,6-trichloro-5-hexenoate and recycling it as a starting material, there was obtained ethyl 1,2,2-trimethyl-3-(2',2'-dichlorovinyl) cyclopropanecarboxylate in an overall yield of 90% based on ethyl 2,3,3-trimethyl-4,6,6-trichloro-5-hexenoate.

EXAMPLE 18

The procedure of Example 10 was repeated except that 40.7 parts of ethyl 3,3-dimethyl-4,6,6-tribromo-5-hexenoate was used in lieu of methyl 3,3-dimethyl-4,6,6-trichloro-5-hexenoate. Thus, the starting material was first treated with a methanolic solution of 6.0 parts of sodium hydroxide to obtain 31.0 parts of a mixture of 2,2-dimethyl-3-(2',2'-dibromovinyl) cyclopropanecarboxylic acid, 3,3-dimethyl-4-(2',2'-dibromovinyl)-4-butanolide and methyl 2,2-dimethyl-3-(2',2'-dibromovinyl) cyclopropanecarboxylate.

This mixture was treated with 40 parts of an ethanolic solution of hydrogen chloride (concentration of hydrogen chloride: about 45%) to obtain 15.3 parts of ethyl 2,2-dimethy- -3-(2',2'-dibromovinyl) clopropanecarboxylate (yield 47%; NMR (100 MHz)δ:1.19 (s), 1.23 (t, J=7 Hz), 1.26 (s) 9 H; 1.53 (d, J=5 Hz) 1 H; 2.08 (dd, J=5 & 8 Hz) 1 H; 4.03 (q, J=7 Hz) 2 H; 6.04 (d, J=8 Hz) 1 H; IR (liquid film): 1600 cm⁻¹ (C=C), 1730 cm⁻¹ (CO)) and 15.2 parts of ethyl 3,3-dimethyl-4-chloro-6,6-dibromo-5-hexenoate (yield 42%).

Then, the latter compound ethyl 3,3-dimethyl-4-chloro-6,6-dibromo-5-hexenoate (15.2 parts) was added to 23.6 parts of starting material ethyl 3,3-dimethyl-4,6,6-tribromo-5-hexenoate and the mixture was subjected to exactly the same procedure as described above. Following the distillation stage, 15.0 parts of ethyl 2,2-dimethyl-3-(2',2'-dibromovinyl) cyclopropanecarboxylate and 15.5 parts of ethyl 3,3-dimethyl-4-chloro-6,6-dibromo-5-hexenoate were obtained. By repeating the procedure of recycling the ethyl 3,3- dimethyl-4-chloro-6,6-dibromo-5-hexenoate concomitantly produced as a starting material, there was obtained ethyl 2,2-dimethyl-3-(2',2'-dibromovinyl) cyclopropanecarboxylate in an overall yield of 81%.

EXAMPLE 19

In 50 parts of methanol was dissolved 6.0 parts of sodium hydroxide. Separately, a mixture of 26.0 parts of methyl 3,3-dimethyl-4,6,6-trichloro-5-hexenoate and 13 parts of methanol was prepared. The methanolic solution of sodium hydroxide was added dropwise under reflux to this mixture over a period of 30 minutes, followed by stirring at that temperature over a period of 30 minutes. The reaction mixture was allowed to cool and neutralized with concentrated hydrochloric acid. The methanol was then distilled off under reduced pressure, whereupon a mixture of oily product and solid sodium chloride was obtained. The solid was dissolved by the addition of water and, then, extracted with diethyl ether. The ether layer was dried over anhydrous magnesium sulfate and the ether was distilled off. The above procedure provided 22.5 parts of a mixture of 2,2-dimethyl-3-(2',2'-dichlorovinyl) cyclopropanecarboxylic acid, methyl 2,2-dimethyl-3-(2',2'-dichlorovinyl) cyclopropanecarboxylate and 3,3-dimethyl-4-(2',2'-dichlorovinyl)-4-butanolide. Then, 100 parts of methanol and 0.1 part of p-toluenesulfonic acid were added to the above mixture, followed by heating under reflux for 20 hours. Thereafter, the methanol was distilled off under reduced pressure, whereupon 21.5 parts of oily product was obtained as a residue. Gas chromatographic analysis showed that it was a mixture of 15.4 parts of methyl 2,2-dimethyl-3-(2',2'-dichlorovinyl) cyclopropanecarboxylate (yield 69%; cis/trans ratio=24:76) and 5.4 parts of 3,3-dimethyl-4-(2',2'-dichlorovinyl)-4-butanolide (yield 26%). This mixture was subjected to distillation under reduced pressure to obtain 13.9 parts of methyl 2,2-dimethyl-3-(2',2'-dichlorovinyl) cyclopropanecarboxylate (b p: 67°–69° C./0.2 mmHg; NMR, δ:1.12–1.25 (m) 6 H; 1.42–2.25 (m) 2 H; 3.60 (s) 3 H; 5.57 (d, J=8.5 Hz), 6.23 (d, J=8.5 Hz)1 H) and 4.7 parts of 3,3-dimethyl-4-(2',2'-dichlorovinyl)-4-butanolide (b p: 94°–97° C./0.4 mmHg; NMR, δ:1.01 (s) 3 H, 1.19 (s) 3 H, 2.13 (d, J=17 Hz) 1 H, 2.43 (d, J=17 Hz) 1 H, 4.78 (d, J=9 Hz) 1 H, 5.95 (d, J=9 Hz) 1 H; IR (liquid film): 1620 cm$^{-1}$ (C=C), 1785 cm$^{-1}$ (CO).

Then, 5 parts of a methanolic solution of hydrogen chloride (concentration of hydrogen chloride: about 50%) was added to 4.7 parts of the latter compound 3,3-dimethyl-4-(2',2'-dichlorovinyl)-4-butanolide, followed by stirring at room temperature overnight. The excess hydrogen chloride and methanol were distilled off under reduced pressure and the residue was further distilled under reduced pressure to obtain 5.6 parts of methyl 3,3-dimethyl-4,6,6-trichloro-5-hexenoate (bp: 80°–82° C./0.3 mmHg; NMR, δ:1.15 (s) 6 H, 2.22 (d, J=15 Hz) 1 H, 2.55 (d, J=15 Hz) 1 H, 3.68 (s) 3 H, 4.93 (d, J=11 Hz) 1 H, 6.10 (d, J=11 Hz) 1 H; IR (liquid film): 1615 cm$^{-1}$ (C=C), 1735$^{-1}$ (CO); yield 96% based on 3,3-dimethyl-4-(2',2'-dichlorovinyl)-4-butanolide.

To 5.6 parts of the methyl 3,3-dimethyl-4,6,6-trichloro-5-hexenoate obtained as above was added a sufficient amount of fresh methyl 3,3-dimethyl-4,6,6-trichloro-5-hexenoate to make a total of 26.0 parts and exactly the same procedure as set forth above was repeated. Following the distillation stage, 14.2 parts of methyl 2,2-dimethyl-3-(2',2'-dichlorovinyl) cyclopropanecarboxylate was obtained. The 3,3-dimethyl-4-(2',2'-dichlorovinyl)-4-butanolide concomitantly produced in the above procedure (4.9 parts) was treated with a methanolic solution of hydrogen chloride to obtain 5.8 parts of methyl 3,3-dimethyl-4,6,6-trichloro-5-hexenoate.

By repeating the above procedure of converting the 3,3-dimethyl-4-(2',2'-dichlorovinyl)-4-butanolide to methyl 3,3-dimethyl-4,6,6-trichloro-5-hexenoate and recycling and adding the latter to starting material on the one hand, and by the procedure of collecting an intermediate distillate between the methyl 2,2-dimethyl-3-(2',2'-dichlorovinyl) cyclopropanecarboxylate and 3,3-dimethyl-4-(2',2'-dichlorovinyl)-4-butanolide fractions, which comprises a mixture of these two compounds, and subjecting this intermediate distillate to distillation under reduced pressure to separate and recover methyl 2,2-dimethyl-3-(2',2'-dichlorovinyl) cyclopropanecarboxylate on the other hand, there was obtained methyl 2,2-dimethyl-3-(2',2'-dichlorovinyl) cyclopropanecarboxylate in an overall yield of about 90% based on the methyl 3,3-dimethyl-4,6,6-trichloro-5-hexenoate employed.

EXAMPLE 20

In 100 parts of methanol was dissolved 16.0 parts of sodium hydroxide. Separately, a mixture of 31.0 parts of ethyl 3,3-dimethyl-4,6,6,6-tetrachlorohexanoate and 30 parts of methanol was prepared. The above methanolic solution of sodium hydroxide was added dropwise to the above mixed solution at the reflux temperature over a period of 30 minutes, followed by stirring at that temperature for 30 minutes. Then, the reaction mixture was allowed to cool and neutralized with concentrated hydrochloric acid. The methanol was then distilled off under reduced pressure to recover a mixture of oily product and solid sodium chloride. The solid was dissolved by the addition of water, followed by extraction with diethyl ether. The ether layer was dried over anhydrous magnesium sulfate and the ether was distilled off. By the above procedure was obtained 21.4 parts of a mixture of 2,2-dimethyl-3-(-b 2-40 ,2'-dichlorovinyl)-cyclopropanecarboxylic acid, methyl 2,2-dimethyl-3-(2',2'-dichlorovinyl) cyclopropanecarboxylate and 3,3-dimethyl-4-(2',2'-dichlorovinyl)-4-butanolide.

To the above mixture was added 100 parts of methanol together with 0.1 part of p-toluenesulfonic acid and the entire mixture was refluxed for 20 hours. The reaction mixture was subjected to distillation under reduced pressure to remove the methanol, whereupon 21.5 parts of oily product was obtained as a residue. Gas chromatographic analysis of the residue revealed that it was a mixture of 9.8 parts of methyl 2,2-dimethyl-3-(2',2'-dichlorovinyl) cyclopropanecarboxylate (yield 44%; cis/trans ratio=25:75) and 10.4 parts of 3,3-dimethyl-4-(2',2'-dichlorovinyl)-4-butanolide (yield 50%). This mixture was subjected to distillation under reduced pressure to obtain 8.8 parts of methyl 2,2-dimethyl-3-(2',2'-dichlorovinyl) cyclopropanecarboxylate (bp: 67°–69° C./0.2 mmHg) and 9.0 parts of 3,3-dimethyl-4-(2',2'-dichlorovinyl)-4-butanolide (bp: 94°–97° C./0.4 mmHg).

To the latter product 3,3-dimethyl-4-(2',2'-dichlorovinyl)-4-butanolide (9.0 parts) was added 10 parts of a methanolic solution of hydrogen chloride (concentration of hydrogen chloride: about 45%) and the mixture was stirred at room temperature overnight.

The excess hydrogen chloride and methanol were distilled off under reduced pressure and the residue was further subjected to distillation under reduced pressure. By the above procedure was obtained 10.8 parts of methyl 3,3-dimethyl-4,6,6-trichloro-5-hexenoate (bp: 80°-82° C./0.3 mmHg; yield 97% based on the 3,3-dimethyl-4-(2',2'-dichlorovinyl)-4-butanolide).

The above methyl 3,3-dimethyl-4,6,6-trichloro-5-hexenoate was treated in the same manner as Example 19, whereby methyl 2,2-dimethyl-3-(2',2'-dichlorovinyl) cyclopropanecarboxylate was obtained in a yield of about 90%.

EXAMPLE 21

The procedure of Example 20 was repeated except that a mixture of 13.7 parts of ethyl 3,3-dimethyl-4,6,6-trichloro-5-hexenoate and 15.5 parts of ethyl 3,3-dimethyl-4,6,6,6-tetrachlorohexanoate was used in lieu of 31.0 parts of ethyl 3,3-dimethyl-4,6,6,6-tetrachlorohexanoate. In the first place, 29.2 parts of the above mixture was treated with 16.0 parts of sodium hydroxide in solvent methanol to obtain 22.1 parts of a mixture of 2,2-dimethyl-3-(2',2'-dichlorovinyl) cyclopropanecarboxylic acid, methyl 2,2-dimethyl-3-(2',2'-dichlorovinyl) cyclopropanecarboxylate and 3,3-dimethyl-4-(2',2'-dichlorovinyl)-4-butanolide.

This mixture was treated with 0.1 part of p-toluenesulfonic acid and 100 parts of ethanol under heating and, then, the ethanol was distilled off. Gas chromatographic analysis showed that the residue was a mixture of 14.2 parts of ethyl 2,2-dimethyl-3-(2',2'-dichlorovinyl) cyclopropanecarboxylate (yield 60% cis/trans ratio=25:75) and 7.3 parts of 3,3-dimethyl-4-(2',2'-dichlorovinyl)-4-butanolide (yield 35%). This mixture was then subjected to distillation under reduced pressure to recover 13.3 parts of ethyl 2,2-dimethyl-3-(2',2'-dichlorovinyl) cyclopropanecarboxylate (bp: 72°-74° C./0.4 mmHg; NMR (100 MHz)δ: 1.12-1.40 (m) 9 H, 1.45-2.30 (m) 2H, 4.12 (q, J=7 Hz) 2 H, 5.63 (d, J=8 Hz), 6.29 (d, J=8 Hz) 1H) and 6.5 parts of 3,3-dimethyl-4-(2',2'-dichlorovinyl)-4-butanolide (bp: 94-97° C./0.4 mmHg).

The latter compound 3,3-dimethyl-4-(2',2'-dichlorovinyl)-4-butanolide (6.5 parts) was treated with 8 parts of an ethanolic solution of hydrogen chloride (concentration of hydrogen chloride: about 45%) to obtain 8.2 parts of ethyl 3,3-dimethyl-4,6,6-trichloro-5-hexenoate (b p: 91°-92° C./0.4 mmHg; NMR (100 MHz)δ: 1.08 (s) 6 H, 1.20 (t, J=7 Hz) 3 H, 2.14 (d, J=14 Hz) 1 H, 2.42 (d, J=14 Hz) 1 H, 4.01 (q, J=7 Hz) 2 H, 4.83 (d, J=11 Hz) 1 H, 5.95 (d, J=11 Hz) 1 H; yield 96% based on 3,3-dimethyl-4-(2',2'-dichlorovinyl)-4-butanolide).

To the above ethyl 3,3-dimethyl-4,6,6-trichloro-5-hexenoate (8.2 parts) was added 5.5 parts of ethyl 3,3-dimethyl-4,6,6-trichloro-5-hexenoate together with 15.5 parts of ethyl 3,3-dimethyl-4,6,6,6-tetrachlorohexanoate. With this mixture as a starting material, the procedure described above was repeated. After distillation under reduced pressure, there was obtained 13.7 parts of ethyl 2,2-dimethyl-3-(2',2'-dichlorovinyl) cyclopropanecarboxylate. The 3,3-dimethyl-4-(2',2'-dichlorovinyl)-4-butanolide (6.3 parts) concomitantly produced in the above procedure was treated with an ethanolic solution of hydrogen chloride to obtain 7.9 parts of ethyl 3,3-dimethyl-4,6,6-trichloro-5-hexenoate.

By repeating the above procedure of converting the 3,3-dimethyl-4-(2',2'-dichlorovinyl)-4-butanolide to ethyl 3,3-dimethyl-4,6,6-trichloro-5-hexenoate and recycling the latter compound on the one hand, and by the procedure of collecting an intermediate distillate between the ethyl 2,2-dimethyl-3-(2',2'-dichlorovinyl) cyclopropanecarboxylate and 3,3-dimethyl-4-(2',2'-dichlorovinyl)-4-butanolide fractions, which comprised a mixture of these two compounds, and subjecting said intermediate distillate to distillation under reduced pressure to separate ethyl 2,2-dimethyl-3-(2',2'-dichlorovinyl) cyclopropanecarboxylate on the other hand, there was obtained ethyl 2,2-dimethyl-3-(2',2'-dichlorovinyl) cyclopropanecarboxylate in an overall yield of about 90% based on the starting material mixture.

EXAMPLE 22

The procedure of Example 19 was repeated exept that 16.8 parts of potassium hydroxide was used in lieu of 6.0 parts of sodiuim hydroxide and that a mixture of 44.1 parts of methyl 3,3-dimethyl-4,6,6-trichloro-b 5-hexenoate and 7.8 parts of methyl 3,3- dimethyl-6,6,6-trichloro-4-hexenoate was used in lieu of 26.0 parts of methyl 3,3-dimethyl-4,6,6-trichloro-5-hexenoate. First, 51.9 parts of the above mixture was treated with 16.8 parts of potassium hydroxide in 200 parts of methanol to obtain 44.5 parts of a mixture of 2,2-dimethyl-3-(2',2'-dichlorovinyl) cyclopropanecarboxylic acid, methyl 2,2-dimethyl-3-(2',2'-dichlorovinyl) cyclopropanecarboxylate and 3,3-dimethyl-4-(2',2'dichlorovinyl)-4-butanolide.

To this mixture was added 0.2 part of concentrated sulfuric acid together with 200 parts of methanol and the mixture was heated, followed by distillation to remove the methanol. Gas chromatographic analysis of the residue revealed that it was a mixture of 29.9 parts of methyl 2,2-dimethyl-3-(2',2'-dichlorovinyl) cyclopropanecarboxylate (yield 67%; cis/trans ratio=25:75) and 10.4 parts of 3,3-dimethyl-4-(2',2'-dichlorovinyl)-4-butanolide (yield 25%). This mixture was then subjected to distillation under reduced pressure to obtain 28.1 parts of methyl 2,2-dimethyl-3-(2',2'-dichlorovinyl) cyclopropanecarboxylate (bp: 67°-69° C./0.2 mmHg) and 9.2 parts of 3,3-dimethyl-4-(2',2'-dichlorovinyl)-4-butanolide (b p: 94°-97° C./0.4 mmHg).

The latter product 3,3-dimethyl-4-(2',2'-dichlorovinyl)-4-butanolide (9.2 parts) was treated with 10 parts of a methanolic solution of hydrogen chloride (concentration of hydrogen chloride: about 50%), whereby 11.0 parts of methyl 3,3-dimethyl-4,6,6-trichloro-5-hexenoate (b p: 80°-82° C./0.3 mmHg) was obtained (yield 96% based on 3,3-dimethyl-4-(2',2'-dichlorovinyl)-4-butanolide).

The methyl 3,3-dimethyl-4,6,6-trichloro-5-hexenoate thus obtained was treated in the same manner as Example 19. By the above procedure was obtained the desired methyl 2,2-dimethyl-3-(2',2'-dichlorovinyl) cyclopropanecarboxylate in a yield of about 90%.

EXAMPLE 23

The procedure of Example 19 was repeated except that ethyl 2,3,3-trimethyl-4,6,6-trichloro-5-hexenoate was used in lieu of methyl 3,3-dimethyl-4,6,6-trichloro-5-hexenoate and that potassium hydroxide was used in lieu of sodium hydroxide. In the first place, 28.8 parts of ethyl 2,3,3-trimethyl-4,6,6-trichloro-5-hexenoate was treated with 8.4 parts of potassium hydroxide in 80 parts of methanol to obtain 22.6 parts of a mixture of 1,2,2-trimethyl-3-(2',2'-dichlorovinyl) cyclopropanecarboxylic acid, methyl 1,2,2-trimethyl-3-(2',2'-dichlorovinyl)

cyclopropanecarboxylate and 2,3,3-trimethyl-4-(2',2'-dichlorovinyl)-4-butanolide.

To this mixture was added 0.1 part of p-toluenesulfonic acid together with 100 parts of ethanol and the mixture was heated. The ethanol was then distilled off. Gas chromatographic analysis of the residue revealed that it was a mixture of 8.3 parts of ethyl 1,2,2-trimethyl-3-(2',2'-dichlorovinyl) cyclopropanecarboxylate (yield 33%) and 13.8 parts of 2,3,3-trimethyl-4-(2',2'-dichlorovinyl)-4-butanolide (yield 62%). This mixture was then subjected to column chromatography (silica gel; elute=n-hexanebenzene=1:1) to isolate 7.5 parts of ethyl 1,2,2-trimethyl-3-(2',2'dichlorovinyl) cyclopropanecarboxylate (NMR,δ: 1.04 (s), 1.13 (s), 1.18 (s), 1.23 (t, J=7 Hz) 12 H; 2.25 (d, J=8 Hz) 1H; 4.08 (q, J=7 Hz) 2 H; 5.57 (d, J=8 Hz), 6.30 (d, J=8 Hz) 1H) and 12.7 parts of 2,3,3-trimethyl-4-(2',2'-dichlorovinyl)-4-butanolide (NMR,δ: 0.78–1.17 (m) 9 H; 2.07–2.53 (m) 1H; 4.71 (d, J=9 Hz), 4.74 (d, J=9 Hz) 1 H; 5.93 (d, J=9 Hz), 5.99 (d, J=9 Hz) 1 H; m p: 58° C.).

Then, the latter product 2,3,3-trimethyl-4-(2',2'-dichlorovinyl)-4-butanolide (12.7 parts) was treated with 30 parts of an ethanolic solution of hydrogen chloride (concentration of hydrogen chloride: about 45%) to obtain 14.2 parts of ethyl 2,3,3-trimethyl-4,6,6-trichloro-5-hexenoate (b p: 104°–106° C./0.4 mmHg; NMR (100 MHz) δ: 1.20 (t, J=9 Hz), 0.9–1.3, 12 H; 2.4–2.7 (m) 1 H; 4.01 (q, J=7 Hz), 4.03 (q, J=7 Hz) 2 H; 4.63 (d, J=11 Hz), 4.78 (d, J=11 Hz) 1 H; 5.96 (d, J=11 Hz), 5.97 (d, J=11 Hz) 1 H; IR (liquid film): 1610 cm$^{-1}$ (C=C), 1730 cm$^{-1}$ (CO)).

With the above ethyl 2,3,3-trimethyl-4,6,6-trichloro-5-hexenoate as a starting material, the procedure described above was repeated to obtain ethyl 1,2,2-trimethyl-3-(2',2'-dichlorovinyl) cyclopropanecarboxylate.

In this manner, the 2,3,3-trimethyl-4-(2',2'-dichlorovinyl)-4-butanolide concomitantly produced was converted to ethyl 2,3,3-trimethyl-4,6,6-trichloro-5-hexenoate, from which an additional amount of ethyl 1,2,2-trimethyl-3-(2',2'-dichlorovinyl) cyclopropanecarboxylate was obtained.

REFERENCE EXAMPLE 1

To a mixed solution of 12.0 parts of sodium hydroxide, 40 parts of water and 60 parts of methanol was added dropwise under reflux 31.0 parts of ethyl 3,3-dimethyl-4,6,6,6-tetrachlorohexanoate and, after the dropwise addition had been completed, the mixture was stirred at that temperature for 2 hours. The reaction mixture was then distilled under reduced pressure to remove the methanol, and the residue was neutralized with hydrochloric acid and extracted with diethyl ether. From this ether layer was obtained 19.2 parts of 3,3-dimethyl-4-(2',2'-dichlorovinyl)-4-butanolide (yield 92%) which had the following properties.
b p: 94°–97° C./0.4 mmHg
IR spectrum (liquid film): 1620 cm$^{-1}$ (C=C), 1785 cm$^{-1}$ (CO)
Mass spectrum: m/e (M+) 208,210,212
NMR spectrum,δ: 1.01 (s) 3 H, 1.19 (s) 3 H, 2.13 (d, J=17 Hz) 1 H, 2.43 (d, J=17 Hz) 1 H, 4.78 (d, J=9 Hz) 1 H, 5.95 (d, J=9 Hz) 1 H
Elemental analysis (Calcd. values in parentheses): C, 46.24 (45.96) %, H, 5.09 (4.82) %

REFRENCE EXAMPLE 2

The procedure of Reference Example 1 was repeated except that 35.4 parts of ethyl 3,3-dimethyl-4-bromo-6,6,6-trichlorohexanoate was used in lieu of ethyl 3,3-dimethyl-4,6,6,6-tetrachlorohexanoate. By this procedure was obtained 19.0 parts of 3,3-dimethyl-4-(2',2'-dichlorovinyl)-4-butanolide (yield 90%).

REFERENCE EXAMPLE 3

To a mixed solution of 6.0 parts of sodium hydroxide, 40 parts of water and 60 parts of methanol was added dropwise under reflux 26.0 parts of methyl 3,3-dimethyl-4,6,6-trichloro-5-hexenoate and, after the dropwise addition had been completed, the mixture was further stirred under reflux for 2 hours. The reaction mixture was then treated in the same manner as Reference Example 1 to obtain 19.5 parts of 3,3-dimethyl-4-(2',2'-dichlorovinyl-4-butanolide (yield 93%).

The above procedure was repeated except that 27.4 parts of ethyl 3,3-dimethyl-4,6,6-trichloro-5-hexenoate was used in lieu of methyl 3,3-dimethyl-4,6,6-trichloro-5-hexenoate. In this case, 19.8 parts of 3,3-dimethyl-4-(2',2'-dichlorovinyl)-4-butanolide was obtained (yield 95%).

EXAMPLE 24

To a mixture of 23.2 parts of 2-methyl-5,5,6-trichloro-2-heptene-4-ol and 32.4 parts of ethyl orthoacetate was 1.0 part of isobutyric acid. The mixture was stirred under a nitrogen atmosphere at 140°–160° C. for 8 hours while the byproduced ethanol was continuously removed from the reaction system. Then, the reaction solution was directly subjected to distillation under reduced pressure to obtain 26.8 parts of oily fraction (bp: 120°–135° C./0.4 mmHg). Gas chromatographic analysis of the fraction revealed that it was a mixture of 20.5 parts of ethyl 3,3-dimethyl-4,6,7-trichloro-5-octenoate (Mass spectrum: m/e(M+) 300, yield 68%) and 5.4 parts of 3,3-dimethyl-4-(2',3'-dichloro-1'-butenyl)-4-butanolide (Mass spectrum: m/e(M+) 236, yield 23%).

Then, 26.8 parts of the above mixture was dissolved in 100 parts of ethanol and, hydrogen chloride gas was bubbled into the solution at room temperature for one hour. It was confirmed by gas chromatography that 3,3-dimethyl-4-(2',3'-dichloro-1'-butenyl)-4-butanolide was no longer detectable in the reaction solution and converted to ethyl 3,3-dimethyl-4,6,7-trichloro-5-octenoate. The low fraction was distilled off and the residue was further distilled under reduced pressure to obtain 26.5 parts of ethyl 3,3-dimethyl-4,6,7-trichloro-5-octenoate (yield 88% based on starting 2-methyl-5,5,6-trichloro-2-heptene-4-ol), the properties of which are given below.
bp: 122°–124° C./0.45 mmHg
IR spectrum (neat): 1730 cm$^1$(CO), 1640 cm$^1$(C=C)
NMR spectrum,δ(ppm): 1.08(s), 1.21(t,J=7 Hz)9H; 1.65(d,J=6.5 Hz)3H; 2.15(d,J=15 Hz), 2.46(d,J=15 Hz)2H; 4.07(q,J=7 Hz)2H; 4.45–4.75(m)1H; 4.94(d,J=10.5 Hz)1H; 6.05(d,J=10.5 Hz)1H

We claim as our invention:
1. A method of producing a γ-halogeno-δ-unsaturated carboxylic acid ester of the general formula:

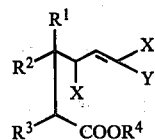

which comprises reacting a γ-lactone derivative of the general formula:

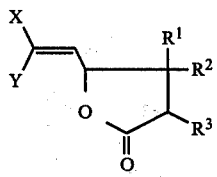

with a hydrogen halide of general formula HX and an alcohol of general formula $R^4OH$, wherein $R^1$ and $R^2$, respectively, mean an alkyl group of 1 to 5 carbon atoms; $R^3$ is selected from the group consisting of hydrogen, alkyl groups of 1 to 5 carbon atoms and cycloalkyl groups of 3 to 8 carbon atoms; $R^4$ is an alcohol residue selected from the group consisting of alkyl, cycloalkyl, alkenyl, cycloalkenyl, alkynyl,

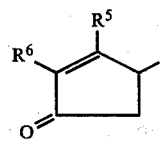

wherein $R^5$ is selected from the group consisting of hydrogen and methyl; $R^6$ is selected from the group consisting of alkenyl, alkadienyl, alkynyl and benzyl,

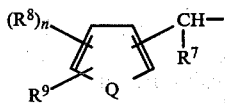

wherein $R^7$ is selected from the group consisting of hydrogen, ethynyl and cyano; $R^8$ is selected from the group consisting of hydrogen, halogen and alkyl; $R^9$ is selected from the group consisting of halogen, alkyl, alkenyl, alkynyl, benzyl, thenyl, furylmethyl, phenoxy and phenylthio; $R^8$ and $R^9$, taken together, may form a polymethylene chain which may be intertupted by a sulfur or oxygen atom; Q is a member selected from the group consisting of —O—, —NH—, —S— and —CH═CH—; n is 1 or 2, A—CH$_2$— wherein A is selected from the group consisting of phenoxyphenyl, phthalimide, thiophthalimids, di- or tetrahydrophthalimido and dialkylmaleimido and

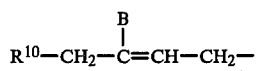

wherein $R^{10}$ is selected from the group consisting of phenyl, thienyl and furyl; B is a halogen atom; and X and Y are halogen atoms which may be the same or different.

2. A method according to claim 1 wherein said γ-lactone derivative is represented by the general formula:

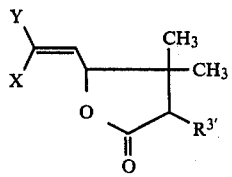

wherein $R^{3'}$ is a member selected from the group consisting of hydrogen and alkyl groups of 1 to 5 carbon atoms; and Xs are the same or different and each means a halogen atom.

3. A method according to claim 1 wherein said alcohol is an alkanol of 1 to 4 carbon atoms.

4. A method according to claim 1 wherein said alcohol is used in a proportion of at least 0.5 times the stoichiometric requirement for a ring-opening esterification of said γ-lactone derivative.

5. A method according to claim 4 wherein the amount of alcohol is 0.5 to 10 times the stoichiometric requirement for a ring-opening esterification of said γ-lactone derivative.

6. A method according to claim 5 wherein the amount of alcohol is 1.5 to 7 times the stoichiometric requirement for a ring-opening esterification of said γ-lactone derivative.

7. A method according to claim 1 wherein said hydrogen halide is used in an amount corresponding to 0.5 to 10 times the stoichiometric requirement for a ring-opening reaction of said γ-lactone derivative.

8. A method according to claim 7 wherein the proportion of hydrogen halide is 1.3 to 5 times the stoichiometric requirement for a ring-opening reaction of said γ-lactone derivative.

9. A method according to claim 1 wherein the ring-opening reaction of said γ-lactone derivative is conducted at temperatures in the range of 0° to 150° C.

10. A method according to claim 1 wherein the unsaturated carboxylic acid ester is produced in a yield of at least about 90%.

11. A method for producing a cyclopropanecarboxylic acid ester of the structural formula:

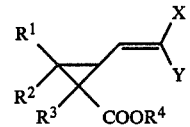

which comprises (i) reacting a γ-lactone derivative of the structural formula:

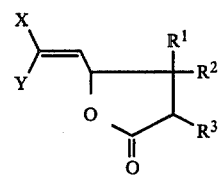

with a hydrogen halide of general formula HX and an alcohol of general formula $R^4OH$ to obtain γ-halogeno-δ-unsaturated carboxylic acid ester of the structural formula:

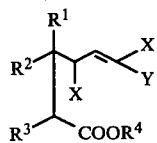

and (ii) treating the so obtained ester with a basic reagent, wherein each of the above formulae $R^1$ and $R^2$ is lower alkyl having from 1 to 5 carbon atoms; $R^3$ is a member selected from the group consisting of hydrogen, lower alkyl having from 1 to 5 carbon atoms and cycloalkyl having from 3 to 8 carbon atoms; $R^4$ is an alcohol residue selected form the group consisting of alkyl, cycloalkyl, alkenyl, cycloalkenyl, alkynyl;

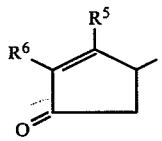

where $R^5$ is selected from the group consisting of hydrogen and methyl; $R^6$ is selected from the group consisting of alkenyl, alkadienyl, alkynyl and benzyl;

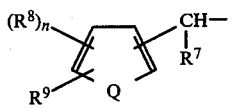

wherein $R^7$ is selected from the group consisting of hydrogen, ethynyl and cyano; $R^8$ is selected from the group consisting of halogen, alkyl, alkenyl, alkynyl, benzyl, thenyl, furylmethyl, phenoxy and phenylthio; $R^8$ and $R^9$, taken together, may form a polymethylene chain which may be interrupted by a sulfur or oxygen atom; Q is a member selected from the group consisting of —O—, —NH—, —S— and —CH=CH—; n is 1 or 2, A—CH$_2$— wherein A is selected from the group consisting of phenoxyphenyl, phthalimido, thiophthalimido, di- or tetrahydrophthalimido and dialkylmaleimido and

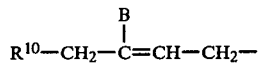

wherein $R^{10}$ is selected from the group consisting of phenyl, thienyl and furyl; B is a halogen atom; and X and Y are halogen atoms which may be the same or different.

12. A method according to claim 11, wherein the γ-halogeno-δ-unsaturated carboxylic acid ester of the structural formula

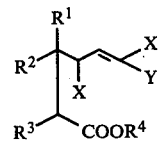

is obtained in a yield of at least 90%.

13. A method according to claim 11, wherein said alcohol is a lower alkanol having from 1 to 4 carbon atoms.

14. A method according to claim 11, wherein said alcohol is used in a proportion of at least 0.5 times the stoichiometric requirement for a ring-opening esterification of said γ-lactone derivative.

15. A method according to claim 14 wherein the amount of alcohol is 1.5 to 7 times the stoichiometric requirement for a ring-opening esterification of said γ-lactone derivative.

16. A method according to claim 11 wherein said hydrogen halide is used in an amount corresponding to 0.5 to 10 times the stoichiometric requirement for a ring-opening reaction of said γ-lactone derivative.

17. A method according to claim 16 wherein the proportion of hydrogen halide is 1.3 to 5 times the stoichiometric requirement for a ring-opening reaction of said γ-lactone derivative.

18. A method according to claim 11 wherein the ring-opening reaction of said γ-lactone derivative is conducted at temperatures in the range of 0° to 150° C.

19. A method according to claim 11 wherein said basic reagent is used in a proportion of 0.3 to 7 moles per mole of the starting material ester.

* * * * *

UNITED STATES PATENT AND TRADEMARK OFFICE
CERTIFICATE OF CORRECTION

PATENT NO. : 4,468,521
DATED : August 28, 1984
INVENTOR(S) : Fumio MORI et al

It is certified that error appears in the above—identified patent and that said Letters Patent is hereby corrected as shown below:

Please change the first inventor's name from "Mori Fumio" to -- Fumio Mori --.

Signed and Sealed this

Thirtieth Day of April 1985

[SEAL]

Attest:

DONALD J. QUIGG

Attesting Officer

Acting Commissioner of Patents and Trademarks